United States Patent
Knight et al.

(10) Patent No.: US 6,323,025 B1
(45) Date of Patent: *Nov. 27, 2001

(54) IN VITRO CELL CULTURE IN MEDIA CONTAINING BETA-ALANYL-TAURINE OR CARBOBENZOXY BETA-ALANYL-TAURINE

(75) Inventors: Galen D. Knight; Terence J. Scallen, both of Albuquerque, NM (US)

(73) Assignee: University of New Mexico, Albuquerque, NM (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/463,784

(22) Filed: Jun. 5, 1995

Related U.S. Application Data

(62) Division of application No. 08/321,010, filed on Oct. 6, 1994, now abandoned, which is a division of application No. 07/941,926, filed on Sep. 8, 1992, now abandoned, which is a continuation-in-part of application No. 07/549,438, filed on Jul. 6, 1990, now abandoned.

(51) Int. Cl.[7] .............. C12N 5/00; C12N 5/02; C12N 5/04; C12N 5/06
(52) U.S. Cl. .......... 435/325; 435/384; 435/404; 435/405; 435/410; 435/420; 435/430.1; 435/245
(58) Field of Search .................... 435/41, 240.2, 435/240.45, 244, 245, 375, 384, 404, 405, 410, 420, 430.1

(56) References Cited

U.S. PATENT DOCUMENTS

| | | | |
|---|---|---|---|
| 2,722,551 | 11/1955 | Snell | 260/561 |
| 4,060,551 | 11/1977 | Uchikuga et al. | 260/561 S |
| 4,102,948 | 7/1978 | Feuer et al. | 260/944 |
| 4,218,404 | 8/1980 | Feuer et al. | 260/944 |
| 4,552,765 | 11/1985 | Mita et al. | 514/513 |
| 4,571,430 | 2/1986 | Byrne | 560/148 |
| 5,370,868 | 12/1994 | Knight et al. | 424/78.08 |
| 6,096,536 | * 8/2000 | Knight et al. | 435/325 |

FOREIGN PATENT DOCUMENTS

| | | |
|---|---|---|
| 2123815 | 2/1984 | (GB) . |
| 508792 | 11/1978 | (HU) . |

OTHER PUBLICATIONS

Weisman et al, "Tricyclic Orthoacetamides and Orthopropionamides: Conformational Analysis and Sterochemical Effects upon $^{13}C$ NMR Spectra", Tetrahdron Letters 22(44):4365–4368 (1981).

Sokolvsky et al, "On the Synthesis of Cystein Peptides", J. Am. Chem. Soc. 86:1202–1206 (1967).

Fifth Report by T. Pantev, "Synthesis of S–(omega–Carboxamidinoalkyl–)–Isothiocarbamides", Nauchnoizski. Inst. Radiobiol. Radiats. Knigy. 5: 57–62 (1975).

Merck Index, #221 (1974).

Garfinkel, "Is Aging Inevitable? The Intracellular Zinc Deficiency Hypothesis of Aging", Med–Hypothesis 19(2):117–37 (1986).

Meister & Anderson, Glutathione, pp. 743–760 (1993).

Chen et al, "The Role of Cholesterol in Malignancy", Prog. exp. Tumor Res. 22:275–316 (1978).

Gilbert, "Molecular and Cellular Aspects of Thiol–Disulfide Exchange", Adv. Enzymol. Metab. Rel. Area 63:69–172 (1990).

Ziegler, "Role of Reversible Oxidation–Reduction of Enzyme Thiols–Disulfides in Metabolic Regulation", Ann. Biochem. 54:305–329 (1985).

Chopra, "Sulfhydryl Groups and the Monodeiodination of Thyroxine to Triiodothyronine", Science 199:904–905 (1978).

Kawachi et al, "Solubilization and Purification of β–Hydroxy–β–methylglutaryl Coenzyme A Reductase from Rat Liver", Biochemistry 9:1700–1705 (1970).

Dotan et al, "Thiol–Disulfide–Dependent Interconversion of Active and Latent Forms of Rat Hepatic 3–Hydroxy–3–Methylglutaryl–Coenzyme A Reductase", Biochemica et Biophysica Acta. 713:427–434 (1982).

Sabine, Chapter 1, "General Distribution and Importance of HMGCoA Reductase", pp. 3–18 (1979).

Rodwell et al, "Regulation of Hepatic 3–Hydroxy–3–Methylglutaryl–Coenzyme A Reductase", Adv. Enzymol. 38:373–412 (1972).

De Flora et al, "Antioxidant Activity and Other Mechanisms of Thiols Involved in Chemoprevention of Mutation and Cancer", The American Journal of Medicine 91:3C–122S (1991).

*Primary Examiner*—David M. Naff

(57) ABSTRACT

Compounds termed "vitaletheine modulators" which include beta-alanyl-taurine and carbobenzoxy beta-alanyl-taurine are synthesized and added to culture media for in vitro culture of cells such as mammalian or plant cells. The compounds support cell vitality, and provide increased cellular life span, increased cellular bioproductivity, improved cellular function, and adaption of resistant cells to culturing. The compounds further delay senescence, optimize growth and maturation, and increase population doublings. Carbobenzoxy beta-alanyl-taurine is produced by coupling β-alanine, which has it's terminal amine protected with a carbobenzoxy (CBZ) group, to N-hydroxysuccinimide to produce an active ester of β-alanine, coupling two of the active esters to cystamine to produce a CBZ-protected β-alethine having an internal disulfide bond, isolating and purifying the CBZ-protected β-alethine, and reacting the CBZ-protected β-alethine with iodine to oxidize the disulfide bond to obtain carbobenzoxy beta-alanyl-taurine. Beta-alanyl-taurine is produced by the same procedure except that after oxidizing with iodine, the carbobenzoxy beta-alanyl-taurine is irradiated with UV radiation to remove the CBZ-protecting group.

14 Claims, 2 Drawing Sheets

OTHER PUBLICATIONS

Roederer et al, "Cytokine–stimulated human immunodeficiency virus replication is inhibited by N–acetyl–L–cysteine", Proc. Natl. Acad. Sci. USA 87:4884–4888 (1990).

Tsao et al, "Glutathione and glutathione S–transferases in clones of cultured rat liver epithelial cells that express varying activity of gamma–glutamyl transpeptidase", Mol. Carcinol. 2(3):144–9 (1989).

Dröge et al, "Modulation of Lymphocyte Functions and Immune Responses by Cysteine and Cysteine Derivatives", The American Journal of Medicine 91:3C–140S (1991).

Eck et al, "Elevated plasma glutamate concentrations in HIV–1–infected patients may contribute to loss of macrophage and lymphocyte functions", Int. Immunol. 1(4):367–72 (1989).

Fraňková, "The Effects Of Amino Acids with Sulfhydryl Groups on Herpes viruses In Vitro", . . . eta virol. 11:559–561, (1967).

Kalebic et al, "Suppression of human immunodeficiency virus expression in chronically infected monocytic cells by glutathione, glutathione ester, and N–acetylcysteine", Proc. Natl. Acad. Sci. USA 88:986–990 (1991).

Eck et al, "Low Concentrations of Acid–Soluble Thiol (Cysteine) in the Blood Plasma of HIV–1–Infected Patients", Biol. Chem. Hoppe Segler 370:101–8 (1989).

Buhl et al, "Systemic Glutathione Deficiency in Symptom–Free HIV–Seropositive Individuals", The Lancet 1294–1297 (1989).

Guder et al, "The Influence of Thyroid Hormones on β–Hydroxy–β–Methylglutaryl–Coenzyme A Reductase of Rat Liver", European J. Biochem. 4:273–278 (1968).

Magee, "Post–translational process of ras proteins", Biochem. Soc. Trans. 19(5):875–6 (1989).

Schafer et al, "Genetic and Pharmacological Suppression of Oncogenic Mutations in RAS Genes of Yeast and Humans", Research Articles, pp. 379–385 (1989).

Gregg et al, "3–Hydroxy–3–Methylglutaryl Coenzyme A Reductase and Cancer", Cholesterol and Cancer, Chapter 17, pp. 245–257 (1982).

Paukovits et al, "Protection From Arabinofuranosylcytosine and n–Mustart–Induced Myelotoxocity Using Hemoregulatory Peptide pGlu–Glu–Asp–Cys–Lys Monomer and Dimer", Blood 77(6):1313–1319 (1991).

Laerum et al, "The Dimer of Hemoregulatory Peptide (HP5B) Stimulates Mouse and Human Myelopoiesis in vitro", Exp. Hematol. 16:274–280 (1988).

Amery et al, "Levamisole and Immunotherapy: Some Theoretic and Practical Considerations and Their Relevance to Human Disease", Oncology 38:168–181 (1981).

Anderson et al, "The Use of Esters of N–Hydroxysuccinimide in Peptide Synthesis", J. Am. Chem. Soc. 86:1839–42 (1964).

Garcia–Peñarrubia et al, "Antibacterial Activity of Human Natural Killer Cells", J. Exp. Med. 169:99–113 (1989).

Dessypris et al, "Increased Sensitivity to Complement of Erythroid and Myeloid Progenitors in Paroxysmal Nocturnal Hemoglobinuria", The New England Journal of Medicine 309(12):690–693 (1983).

Suthanthiran et al, Glutathione rgulates activation–dep. DNA syn. in highly purified normal human T lymphocites stimulated via the CD2 and CD3 antigens, Proc. Natl. Acad. Sci 87:3343 (1990).

Yudkoff et al, "Cysteamine Therapy in Cystinosis", New England J. Med. 304:141 (1981).

Zhang et al, "A Major Inducer of Anticarcinogenic Protective Enzymes from Broccoli: Isolation and Elucidation of Structure" 89:2399 (1992).

Goetz et al, "Clinical Management of Progressive Multifocal Benign and Malignant Melanomas of Horses with Oral Cimetidine", Equine Proceedings, pp. 431–435 (1990).

Amitage et al, The Lancet, Apr. 21, 1979, "Antitumor Effect of Cimetidine".

Thorne, Lynch, Sheehan, "Cimetidine and Coumarin Therapy of Melanoma", The Lancet, Aug. 7, 1982, p. 328.

Osband et al, "Successful Tumor Immunotherapy with Cimetidine in Mice", The Lancet, Mar. 21, 1981, p. 636.

Flodgren et al, "Metastatic Malignant Melanoma: Regression Induced by Combined Treatment with Interferon [HuIFN–α(Le)] and Cimetidine", Br. J. Cancer 32:657 (1983).

Hill et al, Interferon and Cimetidine for Malignant Melanoma, New England J. Med., Feb. 3, 1982, p. 286.

Somogyi et al, "Cimetidine Reduces Procainamide Elimination", N. Engl. J. Med. 307:1080, Oct. 21, 1982.

Currie, "Effect of Autoimmunization with Irradicated Tumor Cells on Specific Cell–Mediated Immunity in Patients with Malignant Melanoma", Proc. Rory. Soc. Med. 65:144 (1972).

Oiry et al, "Synthesis and Radioprotective Activity of New Cysteamine and Cystamine Derivatives", J. Med. Chem. 29(11):2217–2225 (1989).

* cited by examiner

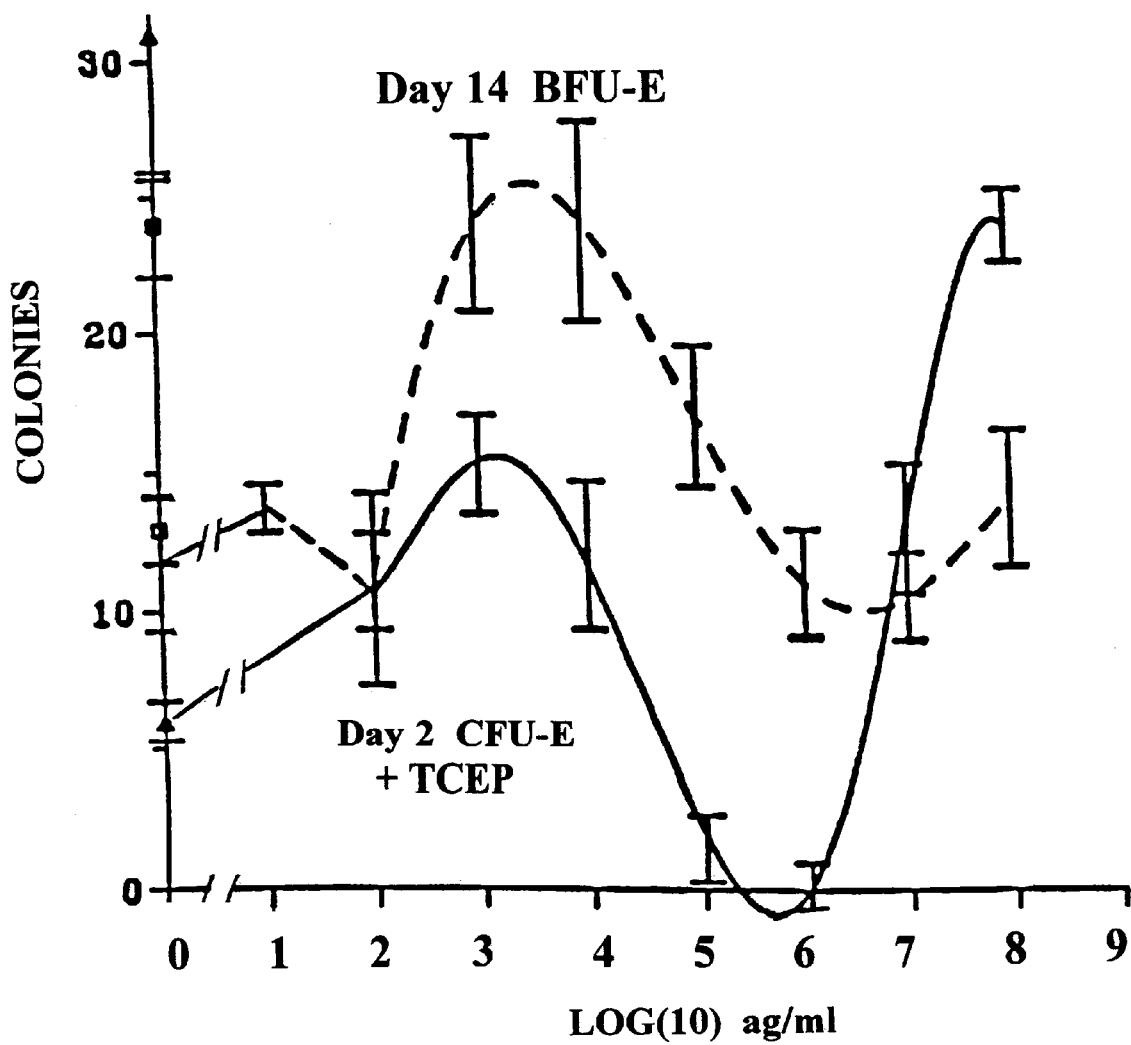

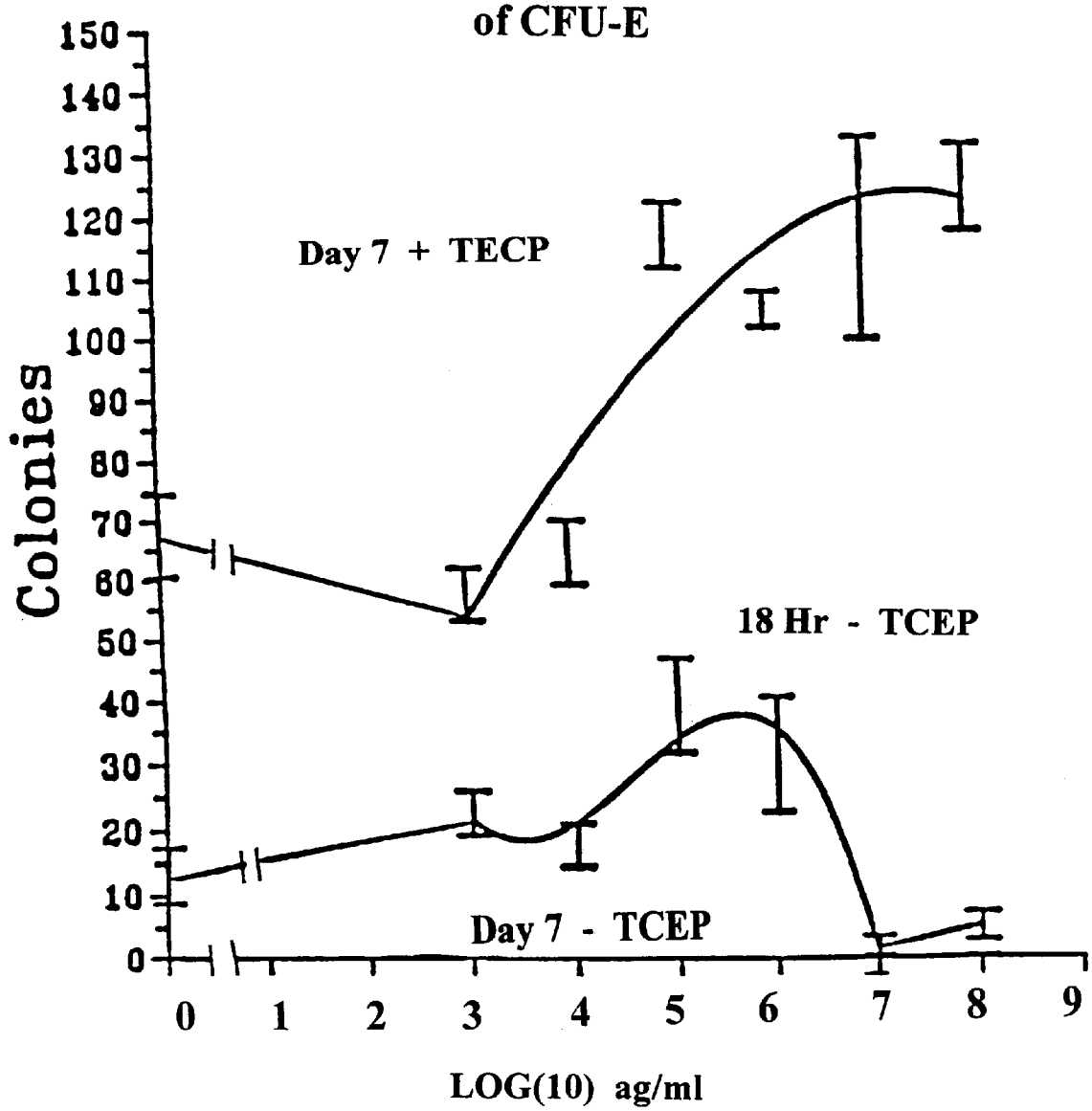

IN VITRO CELL CULTURE IN MEDIA CONTAINING BETA-ALANYL-TAURINE OR CARBOBENZOXY BETA-ALANYL-TAURINE

This application is a division of application Ser. No. 08/321,010, filed Oct. 6, 1994, which is a division of application Ser. No. 07/941,926, filed Sep. 8, 1992, which is a continuation-in-part of application Ser. No. 07/549,438, filed Jul. 6, 1990, all now abandoned.

GOVERNMENT RIGHTS

This invention was made in the performance of work under grants #HL 16,796, #AM 10,628, and #SO7RR-05583-25 with the National Institutes of Health, and the United States Government has certain rights therein.

BACKGROUND OF THE INVENTION

I. Field of the Invention

The invention provides a novel group of compounds for modulating cellular activities comprising sulfur-containing hydrocarbon derivatives of carboxy-amino-amides such as vitaletheine, [N-(2-mercapto-ethane)-3-carboxyamino-propanamide], also designated[N-[3-(2-mercapto-ethanamino)-3-oxo-3,1-propanediyl]-carbamic acid], herein referred to as "vitaletheine modulators". The compounds of the invention are characterized by a pronounced biological activity, and are useful, inter alia, for improving the phenotypic expression and vitality of cells in culture. In particular, the compounds of the invention increase cellular lifespan, increase cellular bioproductivity, improve cellular function in culture, and adapt resistant cells to culture.

"Phenotypic cell expression" is defined herein as the manifestation of an entire range of physical, biochemical and physiological characteristics of an individual cell as determined both genetically and environmentally, in contrast to "genotypic cell expression", which in the art solely refers to the expression of the cell chromosomal sequence. [See, for example, *Dorland's Illustrated Medical Dictionary*, 26th Edition, 1974, W. B. Saunders, Philadelphia]. Biological activity of the vitaletheine modulators of the invention thus includes modulation of the expression of genetic material of cells in culture as influenced by the condition and environment of each cell, including the age of the cell; the culture conditions employed, and the presence of optionally added biological effectors.

2. Discussion of Related Art

Cells which are not capable of continuous growth in culture (non-immortal cells or cell lines) are characterized by a predictable lifespan in vitro, broadly divisible into three phases corresponding to growth, maturation, and decline (i.e., senescence). Cellular senescence is a phenomenon well-recognized in the art, typically characterized, inter alia, by a statistically significant lengthening of the time required for a mature individual cell to reproduce (generation time), by the elongation of normal cell growth patterns reflecting the increasing inability of the cell to efficiently incorporate essential energy and material requirements, and by the termination or statistically significant diminution of the cell's bioproductivity, which is usually optimal at midcycle (maturity). The life spans of many non-immortal cells in culture, particularly mammalian cells, frequently varies from only a matter of hours to only several weeks, even under optimal culture conditions. Sudden, premature death of such cultures is not uncommon. Even so-called immortal cells, such as immortal insect cell lines or mammalian tumor cell lines, tend to lose viability as a function of time in culture, with corresponding decline of the cell mass. Further, many cells, such as mammalian hepatic cells, cannot be presently adapted to long-term culture as a practical matter.

These inherent limitations on cell longevity in vitro have important implications for cultures employed in chemical, industrial, and research applications, and are of particular interest in the in vitro production of mammalian cell products, including recombinant cell products, especially peptides, proteins, and glycoproteins, such as hormones, enzymes, and immunoglobulins, wherein optimum production is typically obtained during the pre-senescent phases of the cell's life-cycle. A variety of methods have been proposed for maximizing the production and longevity of cells within existing limitations imposed by cell growth patterns; these are primarily directed to the improvement of culture conditions by techniques for the rapid replenishment of nutrients and removal of wastes, such as perfusion and continuous culture procedures, or to biological manipulation of cells, such as hybridization with immortalizing cell lines. While such techniques have generally tended to improve bioproductivity in large-scale applications, the improved results are not usually attributable to alteration of cell growth patterns. Further, such prior art methods for improving cell bioproductivities have not been broadly applicable to cells considered non-adaptable to culture; the hepatic cells mentioned above, for example, are currently not maintainable in vitro under known culture conditions for more than a few hours.

Methods for the biochemical modification of cell growth patterns have also been proposed to improve cell propagation, but most have been predicated on the use of cell growth factors. While growth factors as a group generally tend to increase proliferation of cells in culture, cells exposed to these factors also rapidly become exhausted and die, with little or no net gain in cell bioproductivity. Additionally, such growth factors have not been useful in adapting resistant cells to culture.

It is accordingly desirable to provide compounds which are effective for promoting the viability and propagation of cells in culture, particularly for promoting cell vitality, cell bioproductivity, cell function, and cell longevity, and for adapting resistant cells to culture. Such compounds are potentially useful not only by themselves, but also in combination with other bioeffectors which are known to promote cellular propagation, for their contemplated combined effects, such as stabilization and augmentation of the cell biomass.

BRIEF DESCRIPTION OF THE DRAWINGS

FIGS. 1A and B illustrate the effect of vitaletheine modulator on erythropoiesis.

SUMMARY OF THE INVENTION

The invention provides a new group of compounds collectively referred to herein as "vitaletheine modulators": comprising vitaletheine, a free acid or salt of N-(2-mercaptoethane)-[3-(carboxyamino)-propanamide], also designated [N-[3-(2-mercapto-ethanamino)-3-oxo-3,1-propanediyl]-carbamic acid]; vitalethine, the oxidized (or disulfide) form of this compound; biologically-active or -activatable rearrangement forms of these compounds and biologically-compatible salts, hydrates, and oligomers thereof. The modulators of the invention further include biologically-active or -activatable homologs or analogs of vitaletheine or vitalethine and their corresponding rearrangement forms, including salts, hydrates, and oligomers thereof. The compounds of the invention are useful, inter alia, for promoting phenotypic expression and vitality of cells in culture; including, for example, the promotion of increased cellular lifespan in culture, the promotion of increased cellular bioproductivity in culture, the promotion of improved cellular function in culture, and the adaptation of resistant cells to culture. This novel class of compounds thus broadly promote the vitality of cells in culture for a variety of purposes, for example, the efficient and long-term in vitro production of cell products for commercial or research purposes, the clinical comparative study of aberrant and normal cells heretofore resistant to culture, the development and production of transplant tissue or organs in vitro, and, broadly, the culture of cells for previously purely theoretical biomedical applications. The modulators appear to function at least in part by providing a stimulus generic to a broad variety of cells which optimizes cellular production and viability, and provides a starting point for a broad range of contemplated biotechnical, especially biomedical, applications predicated upon effective cell cultures.

DETAILED DESCRIPTION OF THE INVENTION

1. The Compounds:

The compounds of the invention comprise biologically-active or -activatable sulfur-containing hydrocarbon derivatives of a carboxy-amino-amide of the Formula I, hereinafter referred to as "vitaletheine modulators" or "modulators":

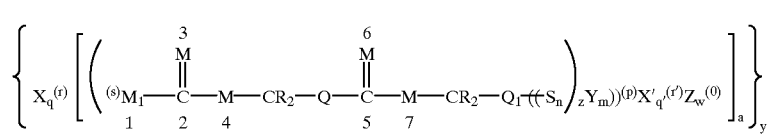

(I)

wherein:

the set of double parentheses brackets the portion of the molecule bearing a charge p when z is 1;

the expression $M_1$—(C=M)—M— (wherein C is the #2C) represents $M_1$—(C=M)—M—, $M_1$=(C—MA)—M—, or $M_1$—(C—MA)=N—, and —(C=M)—M— (wherein C is the #5C) represents —(C=M)—M— or —(C—MA)=N—; wherein A is X, −1, or a direct bond with the proviso that when —(C=M)—M— is —(C—MA)=N— or the compound is polymeric or internal cyclic or spirocyclic, A is optionally R; and M and $M_1$ are as defined below; each R is independently H or a hydrocarbon radical as further defined herein;

X is a biologically-compatible cation or cationic complex as further defined herein;

X' is a biologically-compatible ion or ionic complex as further defined herein;

M is S, O, N, or NH;

$M_1$ is S or O with the proviso that $M_1$ is also optionally N or NH when the compound is polymeric or internal cyclic or spirocyclic;

Q is CR or a direct bond; $Q_1$ is CR, CRCR, or a direct bond;

Y is O, —[C=O]—R, or a direct bond;

$Z^{(0)}$ is a neutral moiety associated with the remainder of the compound of Formula I;

a is the absolute value of $|r/(r'+p+\Sigma s)|$ with the proviso that when $(r'+p+\Sigma s)$ is $\geq 0$, at least one q or q' is zero such that the sum of any charges on the remainder of the complex is balanced by the charges on the ion or ions, X or X', or the ions, X and X'.

m is 0 or a whole integer from +1 to +5;

n is 1 or 2 when z is 1, and n is 1 or 1.5 when z is 2;

p is +1, 0, or −1;

q and q' are each independently +1 or zero;

r and r' are each independently a whole integer from +1 to +4, or r' is a whole integer from −1 to −4;

w is 0 or a whole integer from 1 to 5;

s is −1 or 0;

y is 1 to 40;

z is +1 or +2; and the compound of Formula I has a molecular weight of no more than about 10,000 daltons.

Particularly interesting compounds of the Formula I are those wherein y is from 1 to about 20, especially from about 2 to 10; or wherein the number average molecular weight of the compound is no more than about 5,000 daltons, or both; and especially wherein the molecular weight of the compound is at least about 130 daltons.

Preferred compounds according to Formula I are compounds of the Formula II, herein referred to as "vitaletheine compounds":

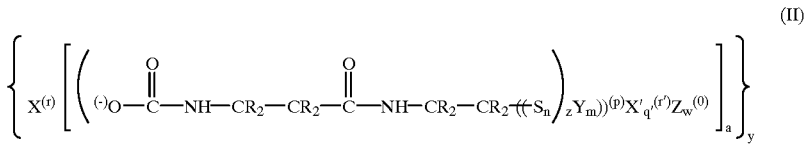

(II)

wherein R, X, X', Y, Z, a, m, n, p, q', r, r', w, y, and z are as defined in Formula I.

The vitaletheine compounds of the invention include compounds of the Formula II in disulfide forms, comprising homologous or heterologous (mixed) disulfides; trisulfide forms, comprising homologous or heterologous trisulfides; and oxidized forms (m>0) of the homologous or heterologous disulfides or trisulfides, wherein z is 2 and n is 1 or 1.5 according to Formula IIa:

$$\left\{X^{(r)}\left[\left((-)O-\overset{O}{\underset{\|}{C}}-NH-CR_2-CR_2-\overset{O}{\underset{\|}{C}}-NH-CR_2-CR_2-S_n\right)_2 Y_m\right]_{r/2}\right\}_y$$

(IIa)

wherein R, X, Y, n, m, r and y are as defined in Formula I.

The vitaletheine compounds of the invention further if include compounds of the Formula II in reduced and oxidized forms wherein z=1, according to Formula IIb:

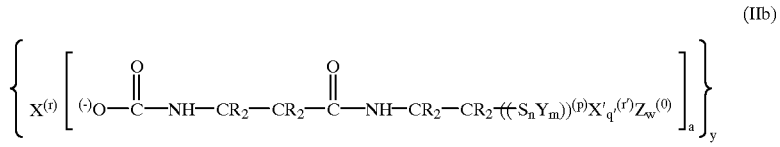

(IIb)

wherein R, X, X', Y, Z, a, n, m, p, q', r, r', w, and y are as defined in Formula II. Particularly contemplated radicals —((S_nY_m))^(P) comprise thioesters and ionized residues of sulfoxy or S-thiosulfoxy acids, especially sulfenic, sulfinic, or sulfonic acids; and when n=2, ionized residues of thiosulfenic, thiosulfoxylic, thiosulfurous, or thiosulfuric acids. Exemplary radicals —((S_nY_m))^(P) include —SOX' (sulfenate), —SX' (thiolate), —SI (sulfenyl iodide), —SI_3 (sulfenyl periodide), S_2O_3X' (thiosulfate); especially SH (thiol or sulfhydryl) and SOH (sulfenic acid). As exemplified above for sulfenyl periodide, a molecule such as I_2 or H_2O, or other neutral moiety may be associated with —((S_nY_m))^(P)X'^(r') or the entire monomer as Z^(0).

The modulators of the present invention include biologically-active or -activatable salts, hydrates, chelates, tautomers, oligomers, and rearrangement forms of the compounds of formulas I, IIa, and IIb, and the corresponding salts, hydrates and chelates of, these rearrangement forms. The rearrangement forms of the compounds are primarily internal 5-or 6-membered cyclization products resulting from nucleophilic attack on susceptible atoms including oxidized sulfur and doubly-bonded carbon atoms arising from the tautomerism of the compounds as illustrated in the following Formula IIc:

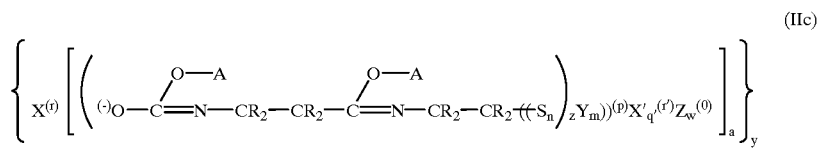

(IIc)

wherein R, X, X', Y, Z, a, n, m, p, q', r, r' w, y, and z are as defined in Formula II; A is R, −1, a direct bond, or X; and either or both of the doubly bonded carbon atoms (2,5) are in the illustrated tautomeric form.

Compounds of the formulas I or II, wherein one or more of the atoms O, M, N, or S are rendered nucleophilic, are readily produced in vivo and in vitro where they tend to form internal cyclization products, typically stabilized by hydrogen bonds (including hydrates), ions (salts or chelates), or both. These cyclic compounds include apparently biologically-inactive but -activatable "storage" forms of compounds of the formula I or II, which are easily rearranged to the corresponding active compound. Compounds of the Formulas I and II and subformulas thereof are typically internally cyclized through S or Y, wherein p is zero, or through M_1—(C=M)—M— or —(C=M)—M—, as illustrated in the Formulas Ia' and Ib' and following formulas:

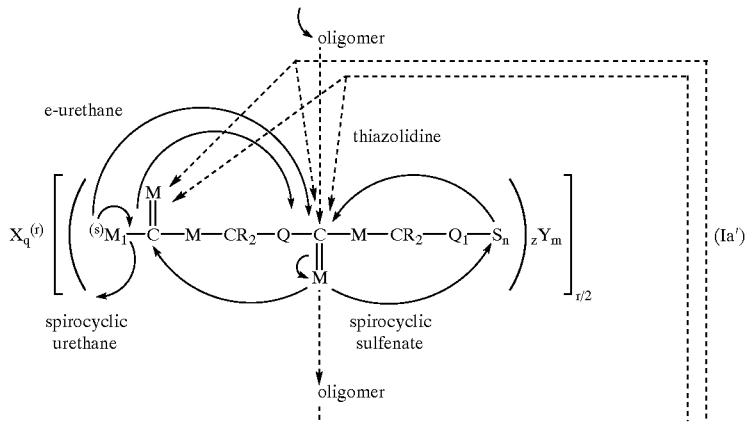

(Ia')

-continued

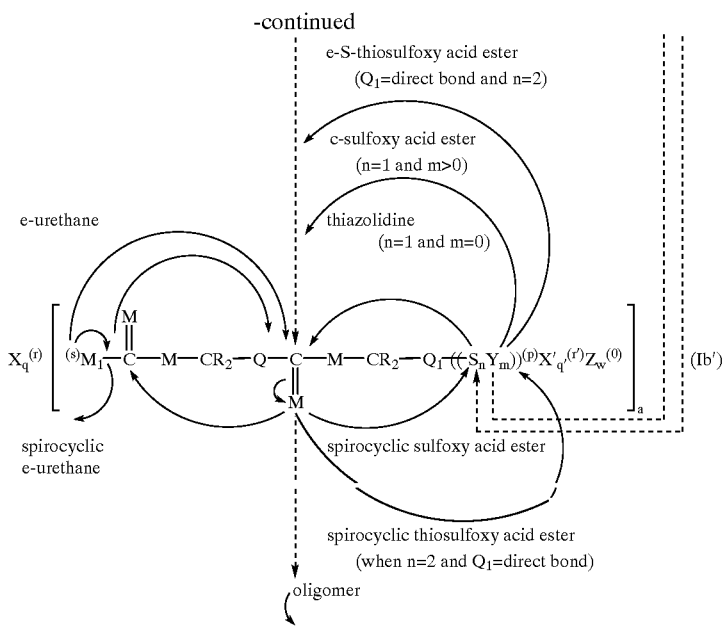

wherein, in the Formulas Ia' and Ib', M, $M_1$, Q, $Q_1$, R, X, X', Y, a, n, m, p, q, q', r, r', s, w, and z are as defined in Formula I; and "c" denotes cyclization.

In general, to form a cyclic urethane of a compound of the Formula I, the charge(s) an the left terminal nucleophile $M_1$ (1) moves to the other nucleophile M (3), either of which may attack the doubly-bonded carbon (5) in the middle of the molecule. The developing charge on the central nucleophile M (6) then picks up an R or X group to form a urethane, or goes on to attack an oxidized sulfur atom, thereby forming a spirocyclic urethane by displacing S as illustrated in Formula Ia'; or by displacing S or Y, and X' or Z or both X' and Z as illustrated in Formula Ib'; in all cases z or n or both are 1 after cyclization of the compound. In a similar fashion, the central doubly-bonded carbon (5) can be attacked by one of the nucleophilic atoms S or Y (Formula Ib'), to produce a thiazolidine, or a sulfoxy or thiosulfoxy acid ester, respectively. In this latter case, a spirocyclic urethane is produced when the resulting charge on the central nucleophile (6) attacks the left terminal doubly-bonded carbon atom (2) resulting in the displacement of, for example, $H_2O$, HAS, or $NH_3$ from the structure. Similarly, the charge or developing charge on either a central or terminal nucleophile (atoms 3 or 6, respectively) permits attack upon another monomer of the Formula I to form a dimer, which in turn is capable of polymerization to an oligomer, as described below.

Compounds of the Formula II, including the subformulas thereof, are referred to herein as "vitaletheine compounds". The reference compound, herein referred to as "vitaletheine", and its oxidized form, herein referred to as "vitalethine", are believed to be the primary biologically-active forms of these compounds. oligomers of vitaletheine containing from about 2 to about 20 monomers, preferably from about 2 to about 10 monomers, and especially from about 2 to 4 monomers are of particular interest, particularly for their stability. Vitalethine is characterized by the structural Formula IId:

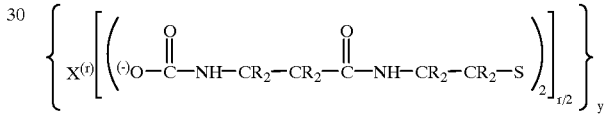

wherein R, X, r, and y are as defined in Formula II. Particularly interesting compounds of the Formula IId are those wherein R is H, and X is $Zn^{+2}$, $Ca^{+2}$, $(CaI)^+$, $(CaOH)^+$, or other cationic complex. The cationic groups and the hydrogen bonding illustrated in the following Formula IId' for vitalethine (y=1) appear to add overall structural stability to the otherwise labile carboxyamino bond:

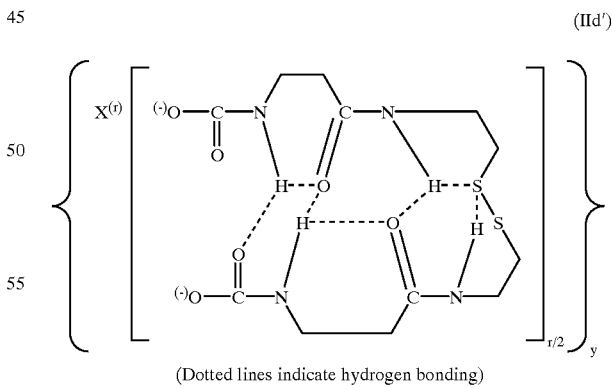

(Dotted lines indicate hydrogen bonding)

Disulfides, sulfenic acids, and sulfenates of Formula I are readily reduced to the corresponding free thiols, particularly in reactions catalyzed by endogenous enzymes, especially reductases and thiol-disulfide isomerases; in particular, vitalethine (Formula IId') is readily reduced to vitaletheine (Formula IIe, wherein R is H and y is 1):

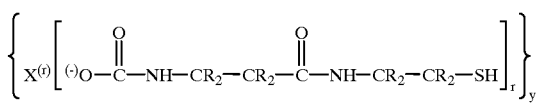
(IIe)

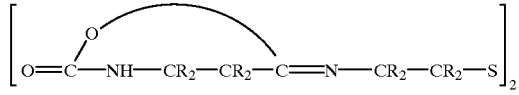
(IIf')

wherein R is as defined in Formula II;

3) a hydroxythiazolidine of the Formula IIg:

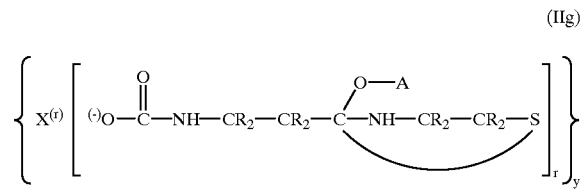
(IIg)

wherein R, X, r, and y in Formulas IId, IId', and IIe are as defined in Formula II. Exemplary preferred cations X include $Zn^{+2}$, $Ca^{+2}$, or a cationic complex such as $(CaI)^+$ or $(CaOH)^+$, especially $Zn^{+2}$. Particularly interesting compounds include oligomers wherein y is from 2 to about 10, especially from 2 to 4, and, more especially, also wherein R is H. Oligomers of the compound of the Formula IIe wherein y is 4 appear to have great biological potency; such oligomers are referred to herein as vitaletheine $V_4$, which refers to compounds of the Formula IIe wherein y is 4, and more particularly refers to compounds of the Formula IIe wherein y is 4, R is H, and X is a calcium or zinc cation, or a cationic complex, as discussed in more detail below.

Exemplary biologically-activatable forms of compounds of the Formula II, which may be activatable in vivo or in vitro or converted to vitaletheine of the Formula IId or IIe, include:

1) a disulfide of a cyclic urethane of Formula IIf:

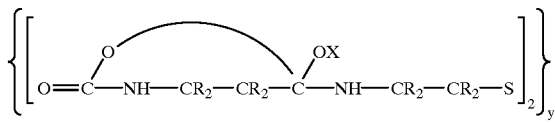
(IIf)

This compound appears to be stabilized as a chelate according to the following model:

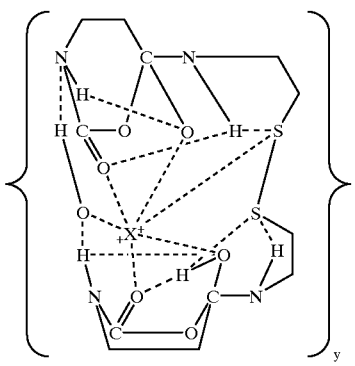

(Dotted lines indicate ionic or hydrogen bonding)

wherein R, X, and y are as defined in Formula II, especially wherein X is $Mg^{+2}$ and wherein the chelate is an $Mg(OH)_2$ chelate;

2) a dehydrate of compound IIf, comprising a cyclic urethane imine of the Formula IIf':

wherein X, R, y, and r are as defined in Formula II and A is R, X, a direct bond, or –1 as defined in Formula IIc;

4) a thiazoline of the Formula IIg', in which Formula IIg is dehydrated to the thiazoline in a manner similar to the dehydration of compounds of the Formula IIf to compounds of the Formula IIf':

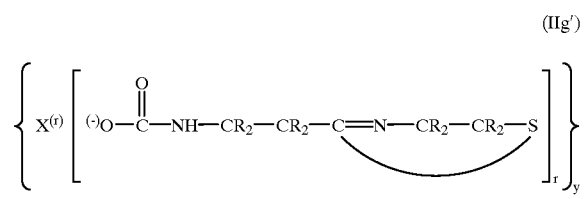
(IIg')

wherein X, R, r, and y are as defined in Formula II;

5) an ionized hydroxythiazolidine of the Formula IIh, as follows:

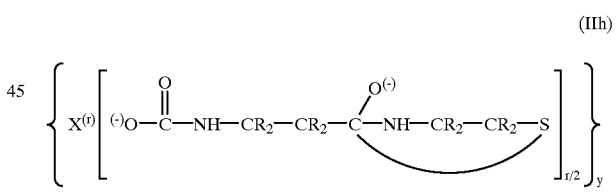
(IIh)

wherein R, X, r, and y are as defined in Formula II; or forms of the thiazolidine of Formula IIh in which the cyclization propagates through the carboxy-amino moiety as in Ia' to form:

a) intermediates of the Formula IIh':

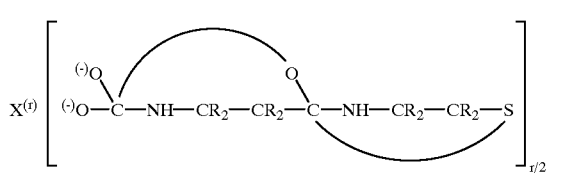
(IIh')

which are dehydratable to:

b) a spirocyclic urethane-thiazolidine of the Formula IIi:

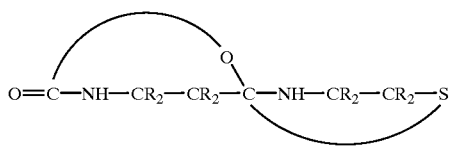

(IIi)

or c) an imidocarbonate tautomer of the Formula IIi':

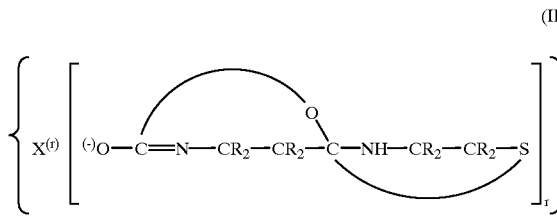

(IIi')

wherein X, R, r, and y in the Formulas IIh', IIi, and IIi' are as defined in Formula II.

Other potentially activatable rearrangement forms of vitaletheine include the following:

6) sulfenates corresponding to the cyclic urethanes of the Formulas IIf and IIf' of the Formulas IIj and IIj':

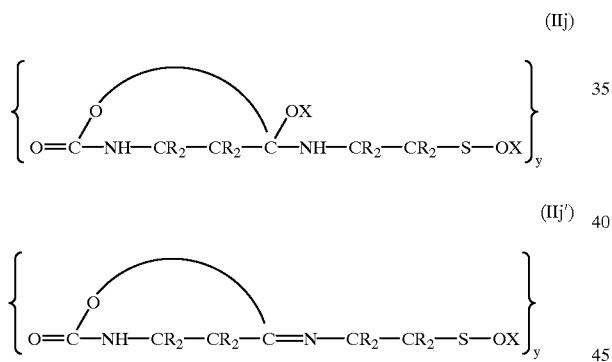

(IIj)

(IIj')

7) cyclic sulfenates corresponding to the thiazolidines of Formulas IIg, IIh, and IIh' of the Formulas IIk, IIm, and IIm':

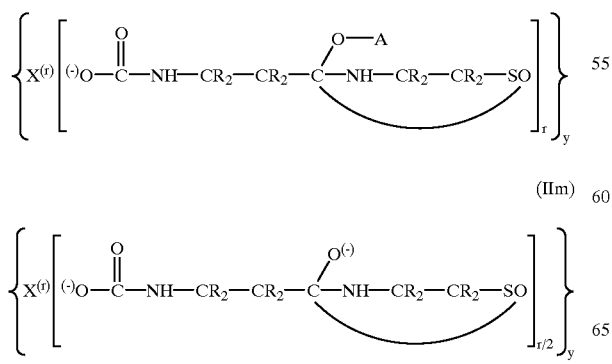

(IIk)

(IIm)

(IIm')

which are dehydratable to:

8) the corresponding dihydro-oxathiazine of Formula IIk':

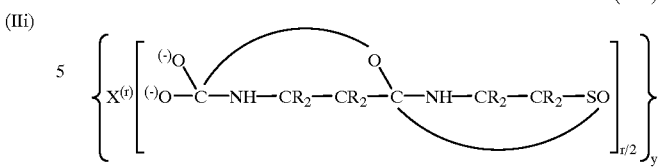

(IIk')

or 9) the corresponding:

a) spirocyclic urethane-sulfenate of the Formula IIn:

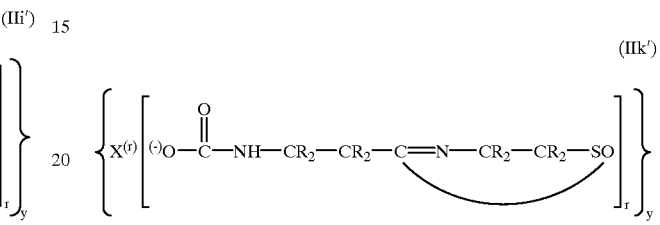

(IIn)

b) or the corresponding imidocarbonate tautomer of Formula IIn':

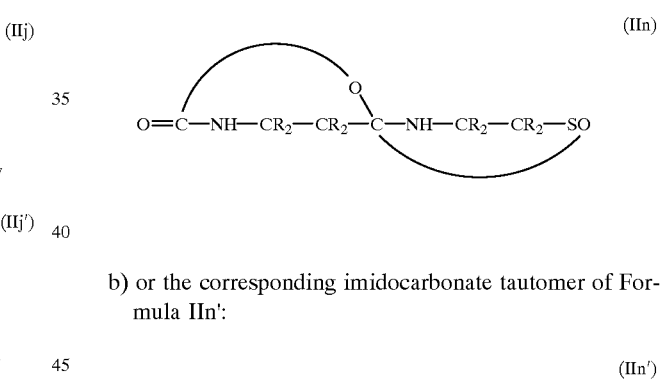

(IIn')

wherein X, R, r, and y in the Formulas IIj through IIn' are as defined in Formula II, and A is as defined in Formula IIc; and the various Formulas II further include rearrangement forms within the scope of the invention as described herein, particularly as described for Formulas Ia' and Ib'.

The modulators of the invention further comprise biologically-active and -activatable derivatives of the vitaletheine modulators of the Formula I, characterized by the following Formula III, herein referred to as "vitaletheine derivatives":

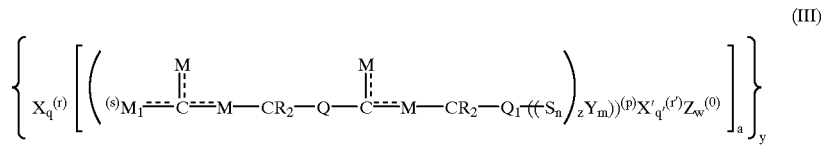

(III)

wherein $M_1$ is S or O; M is S, O, N, or NH; at least one $M_1$ or M is other than O; and R, Q, $Q_1$, X, X', Y, Z, a, n, m, p, q, q', r, r', s, w, y, and z, are as defined in Formula I; wherein the dotted lines are bond resonances or tautomerisms; and wherein in compounds of the Formula III which are internal cyclic and spirocyclic compounds, $M_1$ is additionally optionally M as depicted in Formulas IV through VIe'.

Particular derivatives within the scope of Formula III include homologous or mixed sulfides, homologous or mixed trisulfides, and oxidized forms (m>0) of the homologous or mixed disulfides or trisulfides, wherein z=2 and n is 1 or 1.5 according to Formula IIIa:

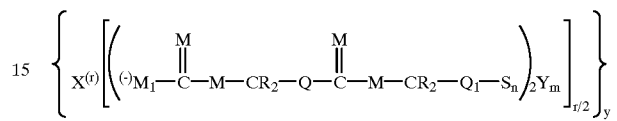

(IIIa)

wherein M, $M_1$, Q, $Q_1$, R, X, Y. m, n, r, and y are as defined in Formula III; and X is especially $H^+$, $Zn^{+2}$, calcium cation, or a calcium cationic complex.

Further derivatives within the scope of Formula III include the reduced and oxidized forms of compounds of Formula III wherein z=1, according to the Formula IIIb:

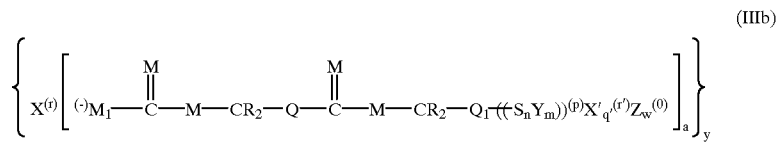

(IIIb)

wherein M, $M_1$, Q, $Q_1$, R, X, X', Y, Z, a, m, n, p, q', r, r', w, and y are as defined in Formula III, and X is especially $H^+$, $Zn^{+2}$, calcium cation, or a calcium cationic complex.

The compounds of the Formula III also include these compounds in the form of their biologically-active or -activatable tautomers, chelates, hydrates, and biologically-compatible salts as described for Formulas I and II, and rearrangement products thereof, including compounds based on nucleophilic cyclization according to Formulas Ia' and Ib'; and further include tautomeric derivatives of compounds of the Formula III as described for Formula IIc, as summarized in Formula IIIc:

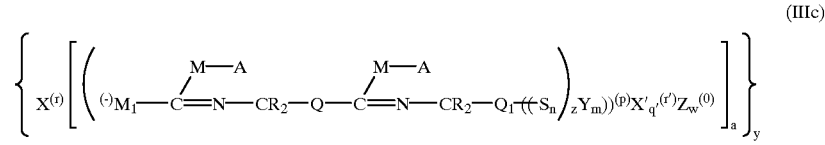

(IIIc)

wherein M, $M_1$, Q, $Q_1$, R, X, X', Y, Z, a, m, n, p, q', r, r', w, y, and z are as defined in Formula III, A is as defined in Formula IIc, and either or both doubly bonded carbon atoms (2,5) are in the illustrated tautomeric form.

Additional compounds within the scope of the invention include modulators of the Formulas IV–VI, and the subformulas thereof, wherein $M_1$ in the compounds of the Formula I is M:

(IV)

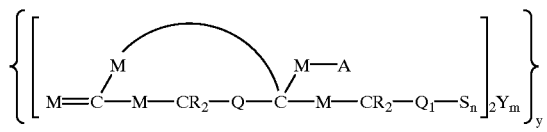

wherein M, Q, $Q_1$, R, Y, m, n, and y are as defined in Formula I and A is as defined in Formula IIc.

Further compounds of the present invention comprise biologically-active and activatable compounds of the Formula V:

(V)

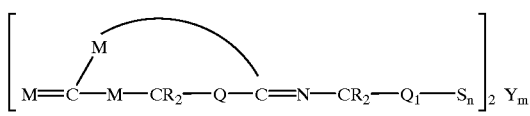

wherein M, Q, $Q_1$, R, Y, m and n are as defined in Formula I.

The compounds of the present invention further include biologically-active and -activatable forms of compounds of the Formulas VI and the following thereof in reduced and oxidized If forms, which comprise:

1) cyclic urethanes of the Formula VI:

(VI)

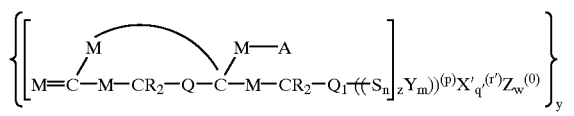

wherein the urethanes are substituted as defined in Formulas IIf, IIg, and IIh; M, Q, $Q_1$, R, X, X', Y, Z, m, n, p, q', r', w, y, and z are as defined in Formula I, and A is as defined in Formula IV;

2) cyclic imines of the Formula VIa comprising urethanes dehydrated as analogously illustrated in Formulas IIf and IIf':

(VIa)

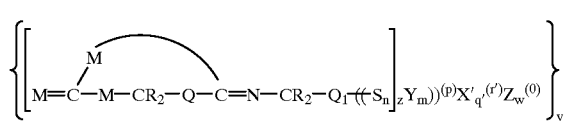

wherein M, Q, $Q_1$, R, X', Y, Z. n, m, p, q, r', w, y, and z are as defined in Formula I;

3) spirocyclic compounds of the Formulas VIb and VIc analogous to precursors of the spirocyclic urethanes of the Formulas IIh' and IIn:

(VIb)

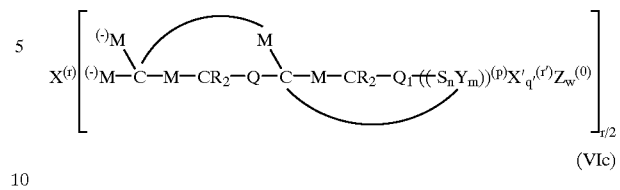

(VIc)

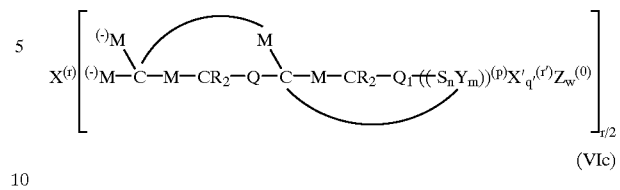

wherein M, Q, $Q_1$, R, X, X', Y, Z. n. m, p, q', r, r', w, and z are as defined in Formula I;

4) corresponding spirocyclic urethane-sulfoxy (n=1) or urethane-thiosulfoxy (n=2) acid esters (Formula VId), or urethane-sulfides (Formula VIe), respectively, formed by elimination of sulfide, nitride, or oxide from the compounds of the Formulas VIb and VIc as $H_2S$, $H_3N$, or $H_2O$:

(VId)

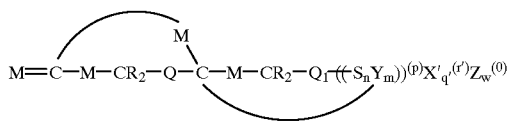

(VIe)

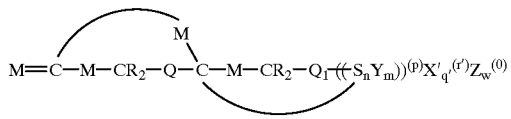

wherein M, Q, $Q_1$, R, X', Y, Z, m, n, p, q', r', and w are defined as in Formula I; or 5) imidocarbonate tautomers of compounds of the Formulas VId or VIe, as described for Formula IIi':

(VId')

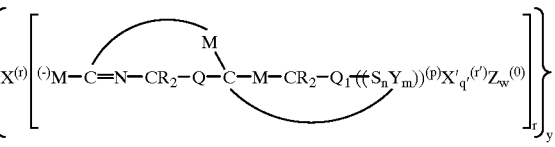

(VIe')

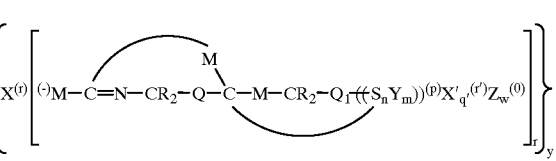

wherein M, Q, $Q_1$, R, X, X', Y, Z, n, m, p, q', r', w, y, and z are as defined in Formula I.

The modulators of the present invention especially include biologically-active or -activatable salts, hydrates, chelates, tautomers, and rearrangement forms of oligomers of monomers of the Formula I, particularly oligomers of monomers of the Formula IId, herein referred to as "vitaletheine oligomers", comprising polymerization products of monomers of the Formula I and subformulas thereof, including cyclizations according to Formulas Ia' and Ib', and the corresponding salts, hydrates, tautomers, and chelates of these forms. Oligomers produced by the polymerization exemplified in Formulas Ia' and Ib' appear to be resistant to rearrangement and provide storage forms of compounds of the invention, which, however, may still be labile to certain organic solvents such as ethers and alcohols. Preferred oligomers of monomers of the Formula I and subformulas thereof are those wherein y is from about 2 to 10. Particularly useful preparations of vitaletheine, include those prepared, for example, according to Example III, especially those comprising a vitaletheine oligomer of 4 monomers (y=4 in Formula IIe and Formula IX following), and particularly optionally including minor proportions of at least one other oligomer or compound of the invention. This tetramer and vitalethine appear to be particularly active. Formation of this oligomer (herein referred to as "$V_4$") appears to occur through an initial nucleophilic attack of a first monomer on one of the doubly-bonded carbons (2,5) of a second monomer to generate a nucleophilic oxygen from the carbonyl oxygen (6) of the second monomer. Polymerization of the monomers of Formula I and the subformulas thereof, for example oligomers wherein y is about 20 or less, appears to be propagated through this initial alkoxide ion (the nucleophilic oxygen 6 resulting from the initial dimerization) until the polymer folds back on itself and the last alkoxide ion present (the fourth in the case of $V_4$) reacts with the first (initiating) monomer. An intermediate dimer, exemplified in Formula VII, is comparable to a benzyl derivative of Formula VIII, obtained as a by-product under certain conditions (see, e.g., Example ZIA) in the synthesis of vitaletheine $V_4$:

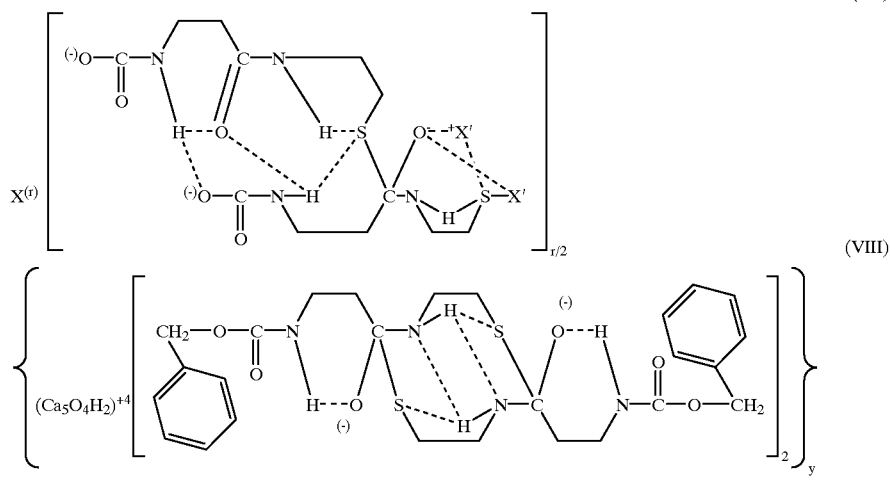

The monomers alternately are linked by Y when Y is the initial attacking nucleophile, according to Formulas Ia', Ib', and X.

The reaction terminating the polymerization is apparently a nucleophilic substitution of the original nucleophile involved in the formation of the first alkoxide ion by the last alkoxide ion, resulting in a cyclic polymer of monomeric subunits, which are nearly identical in spectroscopic analyses. Once formed, the polymer appears to stabilize the carboxy-amino moieties through salt bridges within the oligomer, and sterically prevents rearrangement to other active or activatable forms. Vitaletheine $V_4$ (the tetramer of vitaletheine, Formula IIe) is illustrated in the following Formula IX:

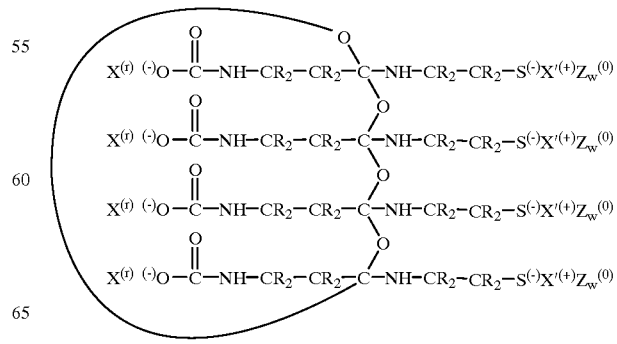

wherein R, X, X', Z, r, and w are as previously defined in Formula I; preferably X or X' is a portion of the cation $Zn^{+2}$ having a charge of +1 and X' or X, respectively, is $H^+$; and especially when X' is a portion of $Zn^{+2}$, X is $H^+$, r is +1, Z is $H_2O$, and w is 2. In the preparation of vitaletheine $V_4$ as described in Example III, 4 $H^+$ and 2 $Zn^{+2}$ neutralize the amino-carboxylate and thiolate charges, and the entire complex contains 8 moles of hydration per mole of complex.

Decomposition or rearrangement of vitaletheine $V_4$ is induced by some organic solvents such as ether, and by heating, which apparently results in decarboxylation of the polymer. Accordingly, caution should be exercised during purification procedures to obviate loss of product.

The modulators of the present invention further include biologically-active and -activatable derivatives of the vitaletheine oligomers of the following Formula X, wherein a compound of Formula III is polymerized as a monomer via nucleophilic attack on one of the doubly-bonded carbons (2,5):

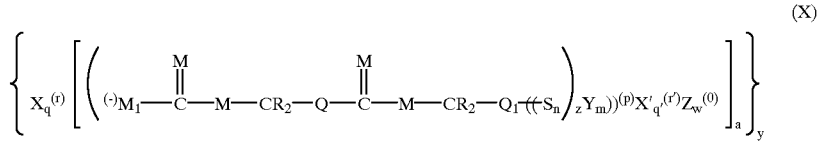

(X)

wherein the attacking nucleophile(s) comprise(s) M1 (1), M (3,6), S, or Y as described for Formulas Ia', Ib', VII, VIII, and IX, and arise through the tautomerizations described herein, particularly as described for Formula IIIc; and wherein M, $M_1$, Q, $Q_1$, R, Y, X, X', Y, Z, r, n, z, m, p, q, q', r', a, w, and y are as defined in Formula I.

In compounds of the Formulas I through X, and the various subformulas thereof, the hydrocarbon radical R is substituted or unsubstituted, saturated or unsaturated, with the provisos that compounds within the scope of the invention have a molecular weight of no more than about 10,000 daltons and contain less than about 40 monomers (y<40); preferably, compounds according to the present invention have a molecular weight of no more than about 5,000 daltons and contain less than about 20 monomers (y<20); most preferably, compounds according to the invention have a molecular weight of at least about 130 daltons; compounds containing from about 2 to 10 monomers are especially interesting. Further, any hydrocarbon substituents R present must not substantially adversely affect the biofunction of the molecule, either chemically or stereochemically.

Preferably, hydrocarbon substituents R comprise suitable lipophilic moieties which counterbalance the hydrophilic portions of the molecule to promote the transfer of the modulators of the invention across the cell membrane to maximize intracellular reactions as understood by those skilled in the art. Further, R is most preferably selected to avoid stereochemical obstruction or biochemical inactivation of the active functional groups of the molecule, particularly the carboxyl-terminus and sulfur-terminus moieties which are apparently critical to the biological function of the molecule, both in their chemical constituents and their physical presentation to the cell. The substituents R are thus not critical to the invention, as long as these groups minimally function as described, do not substantially interfere with the biological activity of the molecule, do not substantially promote decomposition or unwanted side reactions of the molecule, either intracellularly or extracellularly, and do not substantially render the molecule toxic to the cell; such hydrocarbon radicals R are referred to herein as "physiologically-acceptable hydrocarbon radicals R".

Exemplary hydrocarbon substituents R are $C_1$–$C_{20}$-hydrocarbons, especially $C_1$–$C_{18}$-aliphatic or -cycloaliphatic radicals, which are branched or unbranched, substituted or unsubstituted, saturated or unsaturated, particularly $C_1$–$C_{18}$-alkyl or -alkenyl; or substituted or unsubstituted mononuclear or polynuclear aryl, especially phenyl. An exhaustive list of potentially suitable hydrocarbon radicals R is set forth in U.S. Pat. No. 4,216,160 to Doru, et al., incorporated herein by reference, especially the hydrocarbon radicals $R_1$ and $R_2$ described therein. A particularly suitable substituent R is H.

In the compounds of the Formulas I through X, X or X' is $H^+$, hydronium, or a cation or an organic or inorganic cationic complex; or X' is additionally an anion or an organic or inorganic anionic complex; and each X or X' is selected for biological compatibility. The cation or cationic complex X is monovalent, divalent, or polyvalent, especially monovalent, divalent, or trivalent wherein r is +1, +2, or +3; the ion or ionic complex X' is monovalent, divalent, or polyvalent, especially monovalent, divalent, or trivalent wherein r' is −3 to −1 or +1 to +3. X or X' each comprises an ion or ionic complex which does not substantially irreversibly inactivate the active portion of the molecule and which does not substantially interfere with the biofunction of the active remainder of the molecule, either chemically or stereochemically; such ions or ionic complexes X or X' are referred to herein as "biologically-compatible ions". Some ions may inactivate the molecule while they are present, but the inactivation is readily reversed, for example spontaneously, enzymatically, or chemically; such ions or ionic complexes are within the scope of the invention, as it may be convenient to prepare an inactive molecule and subsequently activate it for use, especially in the preparing of molecules targeted for activation and use in specific cells or tissues. Modulators of the invention in solution are highly sensitive to electrolyte concentrations, and are easily irreversibly inactivated by excess amounts of compounds or many electrolytes, particularly magnesium ions. Further, the ions X and X' may shift an existing equilibrium between a biologically-active form of the modulator and a corresponding storage form of the modulator in favor of the storage form, or vice versa. Exemplary cations X which appear to stabilize the molecule in either active or activatable form include $Ca^{+2}$, $(CaI)^+$, $(CaOH)^+$, and especially $Zn^{+2}$, which favor the active form, and $Mg^{+2}$, which may favor an activatable or storage form. Exemplary ions X' include $H^+$, $I^-$, periodide ($I_3^-$), $Zn^{+2}$, or $Ca^{+2}$. As described herein, a charge >+1 on the ion X or X' may be apportioned between two or more negative charges s or p on the remainder of the molecule to form one or more salt bridges within the molecule or between molecules; the "ion X'" in this instance accordingly comprises a portion of the ion X, or vice versa. A positive ion X or X' having a charge greater than +1 may form a bridge between a group bearing a charge of s wherein s is −1 and a group bearing a charge p wherein p is −1 in a given molecule, or between two groups bearing the charge s wherein s is −1, including molecules wherein y=1; or in molecules wherein y>1, they may form a bridge between two groups bearing a negative charge s, or two groups bearing a negative charge p, or between two groups one bearing a negative charge s and the other bearing a negative charge p. When p is +1, an ion X' having a charge less than −1 may also form a bridge between two groups bearing a positive charge in the same molecule. Additionally, an ion X or X' may chelate two identical or different monomers or oligomers of the Formula I. Generally, the total charges on the ions X and X' present will balance the total charges s and p on the molecule; however, in some instances, a portion of the total charge on the molecule may be balanced by one or more ions extraneous to the molecule.

In compounds of the Formulas I through X, the neutral moiety $Z_w(0)$ is a neutral molecule or another neutral moiety which is associable with the compound of the Formula I and subformulas thereof as indicated. Exemplary neutral moieties $Z_w(0)$ include for example, iodine, $H_2O$, polyethylene glycols, and polyoxyethylene ether detergents.

Several inactive but activatable forms of the modulators within the scope of Formula I have been identified, including those described above, which appear in some instances to be inactive "storage" forms of the modulators, capable of in vivo or in vitro rearrangement to one or more active forms. In vivo rearrangement or in vitro rearrangement in the presence of living cells appears to be a result of the action of endogenous enzymes as mentioned above, which, depending upon the type of cell or cells and culture conditions, may convert inactive forms of the compounds of the invention to the corresponding active form, especially in the case of the vitalethine or vitaletheine compounds. Proteins and hydrophobic environments such as cell membranes may associate with and stabilize the active form of the product. Rearrangement of inactive but activatable forms may also be induced by other means as described below.

Within the present context, "biologically-active or activatable" refers to compounds within the scope of Formulas I through X and the subformulas thereof which are biologically active, or which are activatable to biologically active compounds on exposure to activators such as the following: chemicals including biochemicals such as enzymes and selected organic solvents, acids, and bases; radiation including electromagnetic, actinic, or radioactive energy; or heat energy. Inactive compounds which respond to such treatment to become bioactive are referred to herein as "activatable" and are included within the scope of Formulas I through X.

Certain compounds of the invention, and other substances which are postulated to inhibit the degradation or metabolism of the modulators, are useful in combination with the modulators of Formulas I through X. At low concentrations especially, degradation catalyzed by endogenous enzymes represents a mechanism for significant losses of added modulator. Compounds which inhibit these enzymes, without themselves interfering with the action of the modulators, potentiate the action of the modulator by making sustained, low, effective concentrations possible.

II. Preparation of the Compounds:

Compounds according to the present invention, particularly compounds of the Formula IIe wherein R is H, are postulated as endogenous to a substantially complete spectrum of plants, animals, and microorganisms, and, accordingly, it is contemplated that the compounds of the invention are recoverable from a variety of organisms and isolatable for use according to methods well-understood in the art. It is further contemplated that the recited bioapplicability of the compounds to the function of the broad spectrum of cells recited below is attributable to the ubiquitous, or near-ubiquitous presence of these compounds in virtually every living cell and the essential presence of these compounds for the autoregulation of cellular life. However, since the endogenous compounds are thought to be present, in vivo, in extremely small amounts, and are known to be easily converted into inactivatable forms, for example by customary purification methods, it is recommended that the compounds of the invention be synthesized for use, especially to avoid contamination of the product with mitogens, saponins, pathogens, antigens or other potentially reactive compounds present in biological materials, and to prevent the undesirable rearrangements described above.

At present, the most potent of these compounds appear to be those within the scope of Formula IId, viz., those based on the bis anionic vitalethine, [N,N'-(dithiodi-2,1-ethanediyl)-bis-(3-carboxyamino-propan-amide)], also designated as 3,3'-[dithiodi((2,1-ethanediyl) amino]-bis[N-(3-oxo-3,1-propanediyl)-carbamic acid], and polymers of vitaletheine. Analysis of the polymers by filtration through a P-2 gel column indicates that the monomer of vitaletheine (Formula IIe, wherein y is 1 and R is H) tends to spontaneously polymerize during purification to form multimers, especially oligomers wherein y is from 2 to 4; the preparations of the $V_4$ oligomer and vitalethine, especially, have extremely high biological activities.

The [13C]-NMR of vitaletheine $V_4$ (Formula IIe or IX, wherein y is 4 and R is H) indicates nearly homologous subunits; the tetramer (y=4) is an extremely rigid structure similar to those reported for certain ortho-ester-like compounds in Tetrahedron Letters 22:4365–4368 [1981] (incorporated herein by reference). Based on [13C]-NMR analysis, the multimeric vitaletheine structures are postulated to be polymers which are formed by the attack of nucleophilic oxygen (6) derived from the central amide on the carbonyl carbon (5) of another monomer, probably through initial attack of sulfur or atom Y according to Formula X on the carbonyl carbon (5) of the amide of the initiating monomer to generate a nucleophilic oxygen (alkoxide ion) from the carbonyl oxygen (6). Polymerization may be propagated through alkoxide ions in a manner which resembles ortho-ester formation, until the polymer folds back on itself and a terminal alkoxide ion reacts with the original monomer. The polymerization is then terminated by nucleophilic substitution of sulfur or atom Y according to Formula X which initiated the polymerization with a terminal alkoxide ion, resulting in a cyclic polymer which typically contains homologous monomer subunits. Slight puckering of the polymerized $(-C'O-)_n$ ring (n is from about 3 to about 24, usually 3 or 4, especially 4) split observed resonances in the above-described NMR analysis of $V_4$ into four minor peaks in the range calculated for a highly constrained quaternary carbon atom. Polymerization of the monomer does not appear to result from manipulation of the monomer by the applied analytical procedures, since this NMR evidence indicating a tetramer was obtained prior to determination of the molecular weight of the polymer by gel filtration.

Best Modes for Preparing Compounds of the Invention

Although vitalethine is also prepared by the above procedure (Examples IIa and IIIa), carboxylation of β-alethine by reacting the disulfide with phosgene in the appropriate chemical milieu is the preferred method of synthesis. Packing of the reaction vessel in dry ice controls the exothermic reaction and improves yields of large-scale preparations.

Similarities in the physical properties of these two potent biomodulators, i.e. thermal lability and infrared spectra, are described in Examples III, IV, and V.

The compounds of the invention were conveniently prepared employing β-alethine blocked with a protective group such as N,N'-bis-carbobenzoxy-(CBZ—) as starting material. The blocked β-alethine was then selectively deblocked by the process of the invention to remove benzyl groups and yield the compounds of the invention. Techniques for the synthesis of the blocked β-alethine starting material are present in the literature; however, the known techniques generally provided a product of low yield or purity, or both. Many of the impurities obtained in known procedures result from the combined poor solubility of the product compound and the dicyclohexylurea by-product produced in coupling reactions which utilize dicyclohexylcarbodiimide.

According to the process of the present invention, product purity and yield are improved by first coupling CBZ- or similarly-blocked β-alanine to N-hydroxysuccinimide (commercially available from Aldrich Chemicals, Milwaukee, Wis., USA) to produce the corresponding N-hydroxysuccinimide active ester using dicyclohexylcarbodiimide (commercially available from Schwarz/Mann, Orangeburg, N.Y., USA) following the procedure described in J.Am.Chem.Soc. 86: 1839–1842 (1964), incorporated herein by reference. Commercially available starting materials, such as N—CBZ'β-alanine (Sigma Chemical, St. Louis, Mo., USA), are first coupled to N-hydroxysuccinimide (Aldrich Chemicals), with precipitation or the dicyclohexylurea by-product. The soluble active ester product is recrystallized and coupled to the free amino groups of cystamine, readily obtained from cysteamine (available from Aldrich Chemicals) by oxidation with peroxide, for example, by titration in acetonitrile with peroxide until no reducing equivalents are evident. This is conveniently monitored using strips of paper soaked in a solution of 0.1M potassium phosphate buffer and 10 mM 5,5'-dithiobis-2-nitrobenzoic acid (Sigma Chemical) and dried; residual thiol in the peroxide/cysteamine mixture produces an intense yellow spot on the paper. Water added with the peroxide and produced as a by-product of cysteamine oxidation is readily removed by repeated evaporation of the acetonitrile azeotrope prior to coupling with the soluble N-hydroxysuccinimide active ester obtained by dicyclohexylcarbodiimide coupling (supra). Using this form of cystamine instead of a hydrochloride or similar salt ensures more complete reaction of the active ester with the cystamine, since this reaction is dependent upon a nucleophilic attack of the free amines of cystamine on the carbonyl carbon of the active ester. N-hydroxysuccinimide is regenerated as a by-product of this reaction as the blocked β-alethine precipitates. The benzyl groups are then removed from the blocked β-alethine as described, for example, in Examples III and IV, and the product compounds recovered.

III. Utility of the Compounds:

The vitaletheine modulators of the invention are useful, inter alia, for improving cellular phenotypic expression and cellular vitality, in vitro, including, for example, increasing cellular lifespan in culture, increasing cellular bioproductivity, improving cellular function, and adapting resistant cells to culture, especially for enhancing cellular bioproductivity and for adapting resistant cells to culture. The processes of the invention are particularly applicable to those cells not capable of continuous growth under conventional culture conditions, especially "normal" mammalian cells. As defined herein, "normal" cells comprise non-transformed, especially non-virus transformed or non-tumor transformed cells, including non-transformed cells which are functioning abnormally in some respect, such as cells wherein bioproduction levels are abnormally high or low, or functions are either suppressed or aberrantly elevated compared to normal cell functions.

Specifically contemplated utility categories include a) adapting to culture cells which under conventional conditions are substantially resistant to culture, i.e., those cells which have a half-life under conventional culture conditions of less than about two weeks, or which do not express normal products or normal amounts of products in culture; b) obviating the need to fuse cells to immortalizing cells capable of long-term culture in order to obtain extended bioproduction of cell products, such as the current necessity for fusing antibody-producing splenocytes or lymphocytes to immortalizing cells for the en masse production of monoclonal antibodies; c) delaying senescence of cells in culture; d) increasing the viability of cells exposed to growth factors and/or mitogens in culture; e) augmenting the biomass of cells in culture, including stabilizing the cell(s) before, during, and/or after exposure to a proliferative stimulus; f) increasing lifespan of cells in culture; g) enhancing the bioproductivity or function of cells in culture, or both; and h) by increasing the spectrum of phenotypic expression available to cells in culture.

The lifespan of cells in culture is typically characterized in terms of population doubling level (PDL) of the cells, wherein each level represents a new generation of the cells. The time required for a population of cells to double is termed "generation time" (Tg), which varies with the growth stage of a given cell type. Under conventional culture conditions, each cell type has a lifespan characterized by a predictable number of population doubling levels, which are substantially the same for all healthy cells of a given type. Certain human cells, for example, under conventional culture conditions typically double in population from about 40 to 45 times before they senesce and stop normal growth; $T_g$ increases, and death generally occurs at about PDL 50.

In accordance with one aspect of the present invention, the onset of senescence is delayed in cells within the scope of the invention by exposing these cells in conventional growth medium to one or more of the vitaletheine modulators described above. By this process of the invention, the population doubling level attainable by a given cell type in culture before the onset of senescence and death increases significantly. At these high population doubling levels, the cell biomass is greatly increased, and the life expectancy of the cells is significantly extended; an increase from PDL 45 to PDL 105, for example, is achievable for human cells according to this process; this represents an increase in total cell mass as compared to biomass obtainable by conventional culture methods by a factor of $2^{60}$. Further, the peak production period for cellular products is significantly prolonged, with optimization of other cellular functions. Additionally, the vitaletheine modulators of the invention are capable of eliciting enhanced cellular response to chemical, biochemical, or other stimuli, including the expression of functions different or additional, or both, to those expressed by the same type of cells at comparable stages of growth in vivo or under conventional culture conditions.

In order to rectangularize the life cycle of cells in culture, e.g., optimize growth and maturation of cells and minimize the stages of senescence and death, it is preferred that the cells be exposed to the vitaletheine modulators of the invention before the onset of senescence. Since cellular aging is a gradual procedure, senescence may to some degree be arrested even if the cells are exposed to modulator at a later stage in the life of the cells, depending upon the particular cell type, culture conditions, and other factors. However, senescent cells are less viable and productive by definition, so maintaining them at this late stage of the lifespan is counterproductive for most aspects of the invention. Clearly, if the study of senescence is of primary concern then maintenance of the cells at this stage is of interest. Consequently, for optimum results in most instances, it is preferable to expose the cells to modulator as early in their life-cycle as is convenient.

In accordance with an alternate embodiment of the invention, cells which are generally considered not amenable to culture are adapted to culture by exposure to adaptive amounts of the modulators of the invention. Cells within the scope of this embodiment of the invention include cells which have a short lifespan under conventional culture conditions (e.g., from a few hours up to about a few weeks, for example, from about two hours to two weeks), or which do not function normally in culture (e.g., wherein in vivo cell bioproduction of hormones, enzymes, or other bioproducts is partially or substantially completely suppressed in vitro). Normal cells which do not in one or more respects exhibit in vivo behavior in culture, even under optimum culture conditions, as evidenced, for example by a foreshortened lifespan or abnormal cell function, are herein referred to as "resistant cells". Such resistant cells are adaptable to culture by the process of the invention by exposing the cells to be cultured to a vitaletheine modulator according to the invention, ab initio, preferably by incorporating the modulator into the culture medium immediately before or soon after introduction of the cells, depending upon the particular culture medium and the stability of the particular vitaletheine modulator in that medium. By the process of the invention, cellular function of resistant cells in culture is significantly improved, or substantially completely restored to normal cellular function characteristic of in vivo function, and/or cell lifespan is significantly improved or substantially completely restored to at least the cell lifespan characteristic of in vivo lifespans. Further, in accordance with the embodiment of the invention described above, senescence of these cells is generally delayed in the presence of delaying amounts of modulators, often with a concomitant increase in, and potential diversification of, cellular function. Resistant cells within the scope of the invention include a variety of known resistant cell types, for example, lymphoid, hepatic, pancreatic, neural, thyroid, and thymus mammalian cells.

Culture media in which vitaletheine modulators of the invention are to be incorporated for modulation of cell activity of cells cultured therein do not form a part of the invention. Exemplary useful media include all known culture media and media hereinafter developed which support maintenance and/or growth of the cells therein cultured. Such media typically comprise at least nutrients suitable for the growth of the specific cells to be cultured, a physiological balance of electrolytes, a physiological pH, and water, as necessary to support cell growth, as well as physical culture aids such as cell supports. A variety of other known auxiliaries such as antibiotics, sera, or cell growth regulators may also be included in the basal culture media into which the modulators are to be incorporated, especially those known for enhancing cell propagation, or for augmenting cell growth and/or longevity, including cell growth factors such as peptidyl hormones specific for the cells being cultured, of the type well-known in the art. These and other auxiliaries which affect cell longevity and function in some respects are optionally included in the basal culture medium providing that they do not completely obviate the activity of the vitaletheine modulators; in fact, selective proliferation with one or more of these factors, such as, for example, specific peptidyl hormones, in the presence of a vitaletheine modulator to stabilize the cells being generated comprises a useful technique for selectively enriching the cells of interest in a gross cellular extract, for example, organ extracts. Compounds which inhibit metabolism of the modulators may also be included.

Conventional media into which the modulators of the invention are incorporated for the practice of the invention are herein referred to as "basal culture media". Basal culture media into which the modulators of the invention are incorporated may be employed in conjunction with any suitable culture techniques known or hereinafter to be developed, including batch or continuous culture, perfusion culture, or other techniques, particularly those adapted to maximize cell culture, as by the continuous replenishment of nutrients or other media components and continuous removal of cell waste materials.

Broadly, the modulators of the invention are suitable for modulating the activity of cells in any culture medium which supports the growth of these cells and which does not significantly inactivate or otherwise adversely affect the function of the modulators.

The cells to be cultured may be exposed to the modulators of the invention in any convenient fashion. The modulators may, for example, be incorporated into the nutrient medium, or into cell support elements. The cells may also be pre-exposed to modulator. In a particular embodiment of the invention, the modulators are incorporated into a support material by combining the modulators with starting materials employed to prepare the supports. Introduction of modulators into synthetic prepolymers for the production of natural or synthetic supports such as hollow fiber membranes, or pregels for the production of gel supports, or liquefied cellulose for the production of cellulose supports, are exemplary.

Culture media employable with the modulators of the invention include known basal media optionally supplemented with protein components, particularly serum, e.g., fetal or new-born calf serum. Exemplary media include Eagle's Basal Medium; Eagle's Minimal Essential Medium; Dulbecco's Modified Eagle's Medium; Ham's Media, e.g., F10 Medium; F12 Medium; Puck's N15 Medium, Puck's N16 Medium; Waymoth's MB 7521 Medium; McCoy's 5A Medium; RPMI Media 1603, 1634, and 1640; Leibovitz's L15 Medium; ATCC (American Type Culture Collection) CRCM 30; MCDB Media 101, 102, 103, 104; CMRL Media 1066, 1415, 1066, 1415; and Hank's or Earl's Balanced Salt Solution. The basal medium employed, as known in the art, contains nutrients essential for supporting growth of the cell under culture, commonly including essential amino acids, fatty acids, and carbohydrates. The media typically include additional essential ingredients such as vitamins, cofactors, trace elements, and salts in assimilable quantities. Other biological compounds necessary for the survival/function of the particular cells, such as hormones and antibiotics are also typically included. The media also generally include buffers, pH adjusters, pH indicators, and the like.

Media containing the modulators of the invention are applicable to a variety of cells, especially eukaryotic cells. The media of the invention are suitable for culturing animal cells, especially mammalian cells; plant cells; insect cells; arachnid cells; and microorganisms such as bacteria, fungi, molds, protozoa, and rickettsia, especially antibioticproducing cells. The modulators are broadly useful to promote viability of living cells in a broad spectrum of so-called tissue culture media adapted for the culture of such cells. Exemplary applications include the culture of cloned cells, such as hybridoma cell lines; of mammalian cells for the production of cell products, especially proteins and peptides such as hormones, enzymes, and immunofactors; of virally-infected cells for the production of vaccines; of plant cells in, for example, meristem or callus culture; of epithelial cells to provide tissue for wound healing; of resistant cells for medical and diagnostic use; and in media adapted for the production and preservation of biological organs and implant tissue.

Specific cell types useful for culture in the processes of the invention accordingly include: cells derived from mammalian tissues, organs and glands such as the brain, heart, lung, stomach, intestines, thyroid, adrenal, thymus, parathyroid, testes, liver, kidney, bladder, spleen, pancreas, gall bladder, ovaries, uterus, prostate, and skin; reproductive cells (sperm and ova); lymph nodes, bone, cartilage, and interstitial cells; blood cells including immunocytes, cytophages such as macrophages, lymphocytes, leukocytes, erythrocytes, and platelets. Additional cell types include stem, leaf, pollen, and ovarian cells of plants; microorganisms and viruses as specified above; and cells derived from insect or arachnid tissues, organs, and glands.

Culture techniques useful in conjunction with the modulators of the invention include the use of solid supports, (especially for anchorage-dependent cells in, for example, monolayer or suspension culture) such as glass, carbon, cellulose, hollow fiber membranes, suspendable particulate membranes, and solid substrate forms, such as agarose gels, wherein the compound is caged within the bead, trapped within the matrix, or covalently attached, i.e. as a mixed disulfide. The modulators are useful in primary cultures; serial cultures; subcultures; preservation of cultures, such as frozen or dried cultures; and encapsulated cells; cultures also may be transferred from conventional media to media containing the modulators by known transfer techniques.

According to the practice of the invention, cells are exposed to one or more active vitaletheine modulators, or one or more active or activatable modulators, of the Formulas I through X in an amount sufficient to promote culture of these cells in vitro, as measured, for example, by significant increase in cell lifespan, viability, increase in cell biomass, increase in cell bioproductivity, delay of cell senescence, or diversification or normalization of cell function as compared to unexposed cells. Modulators which delay cell senescence or adapt resistant cells to culture are of particular interest.

Modulators useful for promoting culture of cells in vitro according to the invention comprise active- or activatable compounds of the Formulas I through X. As used herein, "active vitaletheine modulators" comprise compounds of the Formulas I through X which per se promote culture of cells in vitro, especially those which directly delay senescence of cells in a given culture and/or adapt cells to culture under the conditions employed. The term "activatable vitaletheine modulators" as used herein refers to compounds of the Formulas I through X which are not in themselves active, but are activatable to compounds which similarly promote culture of cells in vitro, especially those which directly delay senescence and/or adapt cells to culture under the culture conditions employed, primarily by rearrangement including reversible cyclization and tautomerization, dehydration, hydration, salt exchange, oxidation, and/or reduction of the compounds as described herein, either before the modulators are incorporated in the culture medium, or by appropriate adjustment of the culture medium, for example with regard to pH, salt, partial pressure of $O_2$ or $CO_2$, enzyme content, exposure to UV or other radiation, and temperature. The characterization of a given modulator as either "active" or "activatable" for a particular application is dependent on a variety of factors, including culture conditions and cell type, and selection of modulators for optimum results is made accordingly.

In practice, it is generally preferred to employ naturally-occurring vitaletheine modulators of the Formula II and subformulas thereof, as the derivatives thereof of the Formula III, et.seq., are not believed to be endogenous compounds and their metabolic pathways are at present unknown. The naturally-occurring modulators of the Formula II are postulated to be endogenous to a broad spectrum of cells, including animal, plant, insect, arachnid, and microorganism cells, and accordingly, most, if not all, cells derived from these organisms are expected to have well-established mechanisms for the enzymatic activation, utilization, and metabolism of these compounds. Thus, to maximize efficacy and minimize potentially toxic or undesirable side reactions, the use of either naturally-occurring modulators of the Formula I or vitaletheine modulators activatable to the naturally-occurring modulators in the practice of the invention is recommended, especially vitalethine, vitaletheine, or vitaletheine $V_4$ of the Formulas IId, IIe, and IX.

The use of modulators according to the present invention in promoting cell culture in vitro, especially by delaying cellular senescence and/or adapting resistant cells to culture, is contemplated to be applicable to the broad range of cells recited, owing to the postulated near-universality of precursors to the compounds of the Formula II in the metabolic pathways of at least eukaryotic organisms, and the biochemical equivalence of the non-naturally occurring homologs and analogs of Formulas III through VIII.

The effect of the modulators of the invention on cellular growth patterns is typically concentration-dependent. Optimization of efficacy, especially with respect to cell life expectancy and maximization of cell function (e.g., rate of bioproduction and/or diversity or normalization of function) may occur within a relatively narrow concentration range of modulator; outside this range, cell growth patterns and/or cell functions may tend to approach those of conventional cultures. Also, the process of the invention may be, at least in some instances, reversible; that is, cells retained in culture by exposure to the modulators of the invention beyond their normal lifespan may, for example, revert to senescence soon after failure to properly replenish the modulator.

The amount of modulator eliciting the desired cellular response according to the present invention is herein referred to as an "effective amount" of modulator. Optimum amounts of modulator for delaying senescence, herein referred to as "senescence-delaying" amounts, are readily determined by introducing varying amounts of modulator into test cultures substantially before the onset of senescence; and selecting the concentration at which the lifespan of cells in culture is maximized. As previously noted, an amount of modulator sufficient to increase, for example, a selected cell function is often substantially equivalent to the amount of modulator required to effect other modulations of cell activity. Since this may not always be the case, it is useful to adjust modulator concentration against the specifically desired end result; for example, improved rate of cell bioproduction, improved span of cellular bioproduction, improved diversity of cellular function, or improved life expectancy of cells.

The amount of modulator required to adapt resistant cells to culture is herein referred to as an "adapting amount" of modulator. In this instance, the lifespan of resistant cells in culture is significantly improved and cell functions are normalized by at least a threshold amount of modulator. Again, optimal adaptation and/or cell function is conveniently obtained by exposing a series of test cultures to varying concentrations of modulator until the amount of modulator required to satisfactorily grow the cells in culture has been determined. In this embodiment of the invention, excess amounts of modulator will not generally affect adaptation; however, if it is desired, for example, to also delay senescence in accordance with the embodiment by the invention described supra, excess amounts of modulator tending to decrease maximum lifespan, as previously explained, should be avoided.

As a general guideline for effective concentrations of modulator for promoting cellular production according to the invention, especially for promoting cellular phenotypic expression, function, and viability, and particularly for delaying senescence and promoting adaptation of cells to culture, from about 0.01 fg to 100 ng vitaletheine modulator (s) per milliliter culture, and preferably from about 0.1 to 10,000 fg vitaletheine modulators) per milliliter culture is recommended, depending particularly on the potency of the modulator and cell densities. When combinations of the modulators are employed, total amount of modulator will usually be within these ranges. Since the effective amount at the lower concentrations of vitaletheine modulator(s) recited approaches one molecule of modulator per cell, it is especially important to adjust the concentration of modulator at the lower end of these ranges according to the number of cells present in the culture, i.e., the cell density of the culture. Most preferably, the basal culture medium employed is supplemented with sufficient modulator to provide a total concentration of modulator(s) in the medium of from about 1 to 2 fg modulator per milliliter of medium, again depending primarily upon the potency of the modulator, the type of cell, and upon cell densities. Typically, the above concentration ranges of modulator(s) will comprise effective amounts of modulator for cultures irrespective of cell densities, but special problems of nutrient and modulator supply and waste removal exist in confluent cultures. Consequently, confluent cultures should be avoided when possible unless special provisions are made for these environmental needs. Up to ten million cells per milliliter culture is a useful range of cell concentration, for confluency increases at higher cellular densities, again depending upon the size of the cells. Typical cell densities comprise from about one hundred thousand to ten million cells per milliliter culture, and the above described dosages are based upon such densities. Since the effective concentration of modulator has approached one molecule per cell, the concentration of modulator is varied as the concentration of cells increases or decreases.

Replenishment of the vitaletheine modulator(s) to regulate cell activity as desired may be advisable. Diurnal variations in enzymatic activity of modulated cultures are notable, and diurnal or 48 hour replacement is generally recommended for most cultures, typically depending upon the stability of a particular vitaletheine modulator(s) in the particular culture medium and the particular type of cell employed.

Based on illustrated and non-illustrated research data, it appears that cells to be cultured according to the invention may demonstrate an inherent resistance to extra-biological amounts of vitaletheine modulator(s). This is overcome as concentration(s) are increased at a dosage at which a response is first observed, herein referred to as "threshold dosage". The response augments rapidly with dose to a maximum response at a dosage herein referred to as "optimum dosage"; beyond this point, the cell response typically declines with increasing dose to that observed under normal culture conditions. The dosage at which basal senescence is restored is referred to herein as "endpoint dosage". The dosage providing a response from between about the threshold dosage and the endpoint dosage is referred to herein as the "effective concentration or dosage" of the modulator.

Guidelines for the development of dose-response curves for a articular application are conveniently developed as follows:

Dose Response Curve Development Guidelines

A. Employing Vitaletheine Modulator(s) for Delaying Senescence.

Cells of the type to be cultured according to the invention are first grown in a modulator-free control basal culture medium according to standard practice to measure generation time. The onset of senescence is marked by a significant increase in the cell generation time, as well-understood in the art. Samples of the same cell type at chronologically identical stages of development are then cultured in the same medium containing a modulator according to the invention in the amounts ranging for example from about 0.1 femtograms vitaletheine modulator(s) per milliliter to about 1 microgram vitaletheine modulator(s) per milliliter culture medium, based on exemplary cell densities of about one million cells per milliliter culture; preferably, doses of the compound in $\log_{(10)}$ increments are used to localize the effective concentration of any particular vitaletheine modulator. The cultures are then reexamined over a range flanking the effective dosage in less than one $\log_{(10)}$ increments to thoroughly define the effective concentration, the threshold dosage, and the endpoint dosage for that particular culture.

Up to a doubling of the normal lifespan and/or presenescent life of cells in culture is commonly observable according to the process of the invention, and in many instances three-fold or more increases in lifespan are obtainable. Further, cells cultured according to the present process exhibit differences in phenotypic expression, thought to be more characteristic of the cells, in vivo, as compared to untreated cells.

EXAMPLES

Example I

Synthesis of N,N'-bis-(CBZ)-β-alethine {S,SI'-Bis[(N-carbobenzoxy-β-alanyl)-2-aminoethyl]Disulfide}

A solution of dicyclohexylcarbodiimide (23.3 g) was added to a solution of N—CBZ—β-alanine (24.84 g) and N-hydroxysuccinimide (12.92 g) in a total volume of about 500 ml of dry 10% acetonitrile in dichloromethane. Dicyclohexylurea (24.51-g) precipitated as a by-product upon formation of the active ester. The active ester was dried to an oil and triturated with anhydrous ethyl ether. The precipitate was resuspended in dichloromethane and additional dicyclohexylurea was allowed to precipitate. The resulting dichloromethane solution of active ester was filtered and added to a previously prepared solution of cystamine (8.5 g). The desired product, N,N'-bis-(CBZ)-β-alethine precipitated from this mixture. The mother liquor, anhydrous ether and dichloromethane extracts of the product, and the anhydrous ether extract of the active ester, above, were dried and recombined to augment the yield of product. N,N'-bis-(CBZ)-β-alethine was practically insoluble in water, hot ethyl acetate, and hot ether, and these were used to further extract impurities. The product was recrystallized from dimethyl sulfoxide with acetonitrile (or water), and again rinsed with ethyl acetate and ether. This last process resulted in a 1° C. increase in melting point to 180–181° C. (uncorrected). Yields of N,N'-bis-(CBZ)-β-alethine of 85–90% were routinely obtained, and near-quantitative yields are possible. When dried over $P_2O_5$, in vacuo, the product appeared to retain one mole equivalent of water, and was analyzed accordingly as the monohydrate.

Anal. Calcd. for $C_{26}H_{34}N_4O_6S_2 \cdot H_2O$: C, 53.78; H, 6.25; N, 9.65.

Found: C, 54.23; H, 6.56; N, 9.66. Sample analyzed by Ruby Ju, Department of Chemistry, University of New Mexico, Albuquerque, N.Mex.

Example II
Synthesis and Characterization of the Benzyl Derivative of Vitaletheine A. Synthesis The following reagents were added with mixing in the order listed to an Erlenmeyer flask (500 ml): N,N'-bis-(carbobenzoxy)-β-alethine (0.76 g) from Example I, above, dimethyl sulfoxide (0.75 ml), N,N'-dimethylformamide (0.75 ml), pyridine (1 ml), chloroform (21 ml), water (150 ml), and iodine (3.3 g). Upon addition of the iodine the pH began to decrease, and was maintained at 5.7 by slowly adding zinc oxide (0.3 to 0.4 g). It was desirable to maintain this slightly acidic pH to optimize reaction rates. This mixture allowed controlled reaction, continuous extraction of the intermediate product from the organic reagent phase into the aqueous phase, and continuous monitoring of the pH of the aqueous phase. When the reaction began to subside, which was indicated by a stabilization of pH, the aqueous phase was removed and subjected to repeated extractions with chloroform until no color was evident in the organic phase. Periodically during these extractions, the pH was readjusted to 6.0 with a minimum amount of ZnO. When completely extracted and neutralized to pH 6.0, the aqueous phase was dried on a rotoevaporator at low temperature (<40° C.) to a viscous oil. During this process, the organic phase of the reaction mixture was re-extracted with water to recover residual intermediate product, which was subsequently extracted with chloroform, neutralized with ZnO, and dried with the first aqueous extract.

This stage in the synthesis represents a branch point for the synthesis of the desired compound; at this point, either the desired compound or the benzyl derivative thereof can be obtained. For example, either vitaletheine $V_4$

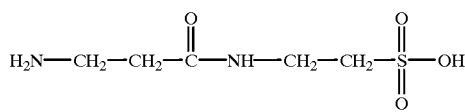

(Example III) or the benzyl derivative of vitaletheine

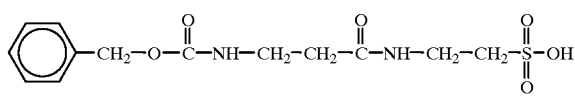

can be produced at this stage.

To obtain the benzyl derivative of vitaletheine, the aqueous extracts obtained as above were treated with ten volumes of acetonitrile to precipitate the benzyl derivative as the primary product.

B. Characterization of the Benzyl Derivative of Vitaletheine

The benzyl derivative obtained above had approximately the same molecular weight as the blocked alethine starting material. However the derivative was unlike N,N'-bis-(CBZ)-β-alethine in many respects: it was soluble in water; it had unique [$^{13}$C]- and [$^{1}$H]-NMR spectra; and its IR spectrum was likewise distinct. The benzyl derivative was purified as the calcium salt, but this difference from the zinc salt of vitaletheine $V_4$ (below) could not account for the extremely high melting point of the former; the benzyl derivative melted at temperatures in excess of 300° C., while the starting material melted at 180–181° C. (uncorrected). The NMR spectra of the zinc and calcium salts of the benzyl derivative were quite similar, evidence that salts alone could not account for these differences.

The spectra of the benzyl derivative were not consistent with thiazolidine or cyclic-urethane structures, and no detectable disulfide or thiol was present, suggesting that like vitaletheine $V_4$, the benzyl derivative was formed by the nucleophilic attack involving sulfur on one of the carbonyl carbons in each monomer. Unlike vitaletheine $V_4$, the predominant polymer in the product benzyl derivative was identified as a dimer, probably formed by attacks of each monomer on the carbonyl carbon of the other, as described above. The quaternary carbons present appeared identical, and were not shifted upfield (**) in the NMR spectrum, in contrast to the pronounced upfield shift of the quaternary carbon atoms present in the vitaletheine tetramer, indicating fewer structural constraints in the benzyl derivative dimer than in the vitaletheine tetramer. Elemental analysis indicated additional material had crystallized with the benzyl derivative, and good correlation was found for inclusion in the dimer of 2 mole equivalents of calcium ion and one mole equivalent of oxygen per mole of the dimer. This was consistent with the presence of a calcium oxide bridge between two dimers, stabilized by hydrogen bonding. The following was the result of elemental analysis for the benzyl derivative obtained above, correcting for the presence of the calculated oxygen and calcium ion:

Anal. Calcd. for $C_{26}H_{34}N_4O_8S_2 \cdot 2\ Ca^{++}O^=$: C, 45.20; H, 4.96; N, 8.11.

Found: C, 44.97; H, 4.98; N, 8.04. Sample analyzed by Ruby Ju, Department of Chemistry, University of New Mexico, Albuquerque, N.Mex.

Example III
Synthesis and Characterization of Vitaletheine Vi.

A. Synthesis.

The benzyl group was removed by repeatedly exposing the dried aqueous extracts obtained in Example IIA to ultraviolet light (Pen-ray quartz lamp, Ultra Violet Products, Inc., Cambridge, U.K.) and extracting with chloroform until no color developed under UV irradiation, and no color was extractable into chloroform. UV irradiation is particularly recommended for effectively obtaining product substantially devoid of aromatic moieties, without causing more serious and inactivating rearrangements and decompositions, as described previously. The product (when completely free of aromatics) was dried, neutralized in water with ZnO, and recrystallized from dimethylsulfoxide with acetonitrile to yield the zinc salt of vitaletheine $V_4$.

B. Characterization of Vitaletheine $V_4$

Vitaletheine $V_4$ was likewise distinct with reference to both the starting material and the benzyl derivative. Obtained in greater than 50% yield from the above procedure, it melted with decomposition at 233–235° C. (uncorrected). Evolution of gas signified decomposition of the molecule; the evolved gas ($CO_2$) was trapped by bubbling through a saturated solution of $Ba(OH)_2$ under $N_2$, with recovery of $BaCO_3$. Decomposition of the molecule on heating was consistent with the presumptive thermal lability of the postulated carboxyamino structure, as was the evolution of $CO_2$ upon heating, and the recovery of the trapped $CO_2$ as the insoluble barium carbonate. The possibility that the evolved gas resulted from decomposition of zinc carbonate contaminating the vitaletheine $V_4$ was deemed unlikely, since this salt decomposes with $CO_2$ evolution at 300° C. The spectral evidence likewise indicated a structure unique to vitaletheine $V_4$, comprising covalent attachment of the carbon in question (2) to the β-aletheine moiety. Concomitant with the evolution of $CO_2$, losses of a sharp N-H stretch resonance at 3290 $cm^{-1}$ and other resonances associated with the carboxyamino structure were observed in the IR spectra.

Vitaletheine $V_4$ as prepared was somewhat hygroscopic, possibly exacerbated by residual dimethylsulfoxide. The following elemental analysis reflected the propensity of the molecule to gain water:

Anal. Calcd. for $CH_{24}H_{44}N_8O_{12}S_4 \cdot 2\ Zn^{++} 8\ H_2O$: C, 27.72; H, 5.82; N, 10.78. Found: C, 28.56; H, 5.94; N, 10.96. Sample analyzed by Ruby Ju, Department of Chemistry, University of New Mexico, Albuquerque, N.Mex.

The results of several different analyses indicated that the vitaletheine dimer contained 1 $Zn^{+2}$, the trimer contained 1.5 $Zn^{+2}$, and the tetramer contained 2 $Zn^{+2}$ per mole of polymer.

Example IV
Synthesis and Characterization of Vitalethine via β-alethine.

A. Synthesis of β-alethine 2HCl or N,N'-bis-(β-alanyl)-cystamine or N,N'-bis-(β-alanyl-2-aminoethyl) disulfide. Complete removal of the carbobenzoxy group was accomplished according to procedures described in *J.Am.Chem..Soc.* 86: 1202–1206 (1964), incorporated herein by reference. After deblocking with four equivalents of hydrogen bromide in glacial acetic acid per mole of the N,N'-bis-(CBZ)-β-alethine (from Example I, above) for 15 hours, the δ-alethine was purified by precipitating with acetonitrile, rinsing with anhydrous ethyl ether, resuspension in water and filtering, and precipitating the mixed salts with acetonitrile. Initial yields were in excess of 80% theoretical. The β-alethine was converted to the hydrochloride salt by passing the preparation over a 30 ml×15 cm long column of Dowex AG 1×8 (chloride form) (Dow Chemical Corp., Midland, Mich.) which had been previously prepared by eluting with 1 M potassium chloride and rinsing thoroughly with DI (deionized) water. Neutralization with $Ca(OH)_2$ and recrystallization of the β-alethine hydrochloride from water with acetonitrile resulted in fine needles which melted at 224–225° C. (uncorrected).

Anal. Calcd. for $C_{10}H_{22}N_4O_2S_2 \cdot 2HCl$: C, 32.69; H, 6.59; N, 15.25.

Found: C, 32.52; H, 6.69; N, 15.32. Sample analyzed by Ruby Ju, Department of Chemistry, University of New Mexico, Albuquerque, N.Mex.

B. Synthesis of Vitalethine

To a suspension of ZnO (6.5 mg from King's Specialty Company, Fort Wayne, Ind., U.S.A.) and β-alethine (6.35 mg from Example IV. A. above) in pyridine (12.6 mg from Fisher Scientific, Fair Lawn, N.J., U.S.A.) and dimethylsulfoxide (0.5 ml from Sigma Chemical Company, St. Louis, Mo., U.S.A.), and in a vessel equipped with a gas trap containing sodium hydroxide (at least 1M), was added 0.2 ml of a solution of phosgene (20% in toluene from Fluka Chemical Corp, Ronkonkoma, N.Y., USA). Packing of the reaction vessel in dry ice controls the exothermic reaction and improves yields of large-scale preparations. After 48 hours of reaction the excess phosgene was blown into the alkali trap with $N_2$. The product was precipitated in the vessel with acetonitrile (approximately 50 mls from Fisher Scientific, Fair Lawn, N.J., U.S.A.). Vitalethine can be recrystallized from water with acetonitrile.

C. Characterization of Vitalethine

Unlike the starting material, β-alethine which melted at 224–225° C. (uncorrected), the vitalethine powder sintered and turned brown at 215–220° C., but did not melt until 242° C. (uncorrected) at which point obvious decomposition and evolution of gas occurred. This behavior resembled that of vitaletheine $V_4$, in that gas was also evolved upon melting of the polymer. The infrared spectrum of the two compounds were likewise similar, but the vitalethine spectrum did not exhibit the C—O stretch bands observed in the polymer. Both compounds lost infrared resonances associated with the carboxy-amino group upon thermally labilizing this moiety. This was particularly true of vitalethine, for major peaks disappeared at 1600 and 1455 $CM^{-1}$ (resonances for the ionized carboxylic moiety), and losses in the fine structure in the regions 2800 to 3300 $CM^{-1}$ and 900 to 1360 $CM^{-1}$ (i.e., those associated with the N—H and C—N moieties of the carboxy-amino group) were also apparent upon heating at 242° C.

EXAMPLE V

[$^{13}C$]-NHR, [$^1H$]-NHR, and IR Spectra of Vitalethine, $V_4$ and Related Compounds

| | a<br>S—$CH_2$ | b<br>$CH_2$—N | c<br>H—N—C=O | d<br>O=C—$CH_2$ | e<br>CH2—N | f<br>H—N—C=O<br>\\<br>O⁻ |
|---|---|---|---|---|---|---|
| β-alethine | 37.59 | 39.04 | 172.79 | 32.9 | 36.71 | |
| Vitaletheine $V_4$ | 36.66 | 35.93 | 47.06*44.75<br>39.41*38.51 | 50.39 | 32.96 | 172.73 |
| Benzyl derivative | 33.79 | 35.76 | 156.46** | 48.36 | 34.67 | 172.25 |

[$^{13}C$]—NMR

-continued

[1H]—NMR

| | a<br>S—CH$_2$ | b<br>CH$_2$—N | c<br>H—N—C=O | d<br>O=C—CH$_2$ | e<br>CH$_2$—N | f<br>H—N—C(=O)—O$^-$ |
|---|---|---|---|---|---|---|
| β-alethine* | 2.524 | 3.094 | | 2.694 | 3.367 | |
| β-aletheine (Zn$^{++}$) | 2.512 | 3.084 | | 2.695 | 3.372 | |
| β-aletheine (+I$_2$) | 2.512 | 3.087 | | 2.687 | 3.366 | |
| Vitaletheine | | | | | | |
| V$_4$ (D$_2$O) | 2.502 | 3.081 | | 2.937 | 3.416 | |
| (DMSO-D$_6$) | 2.200 | 2.763 | 7.84 | 2.418 | 3.131 | 7.38 |
| Benzyl-derivative | | | | | | |
| (D$_2$O) | 2.232 | 3.201 | | 2.841 | 3.330 | |
| (DMSO-d$_6$) | 2.210 | 3.176 | 7.84 | 2.593 | 3.309 | 7.247 |
| bis-(CBZ)-β-alethine (DMSO-D$_6$) | 2.740 | 3.309 | 8.085 | 2.254 | 3.192 | 7.24 |
| Reductase Factor (Inactive) | 2.71 | 3.08 | | 2.90 | 3.28 | |

| | S—CH$_2$<br>a | CH$_2$—N<br>b | H—N—C=O<br>c | O=C—CH$_2$<br>d | CH$_2$—N<br>e | H—N—C(=O)—O$^-$<br>f |
|---|---|---|---|---|---|---|

IR (cm$^{-1}$)

| | a<br>S—CH$_2$ | b<br>CH$_2$—N | c<br>H—N—C=O | d<br>O=C—CH$_2$ | e<br>CH$_2$—N | f<br>H—N—C(=O)—O$^-$ |
|---|---|---|---|---|---|---|
| Vitalethine | | | 3170w<br>1550w | | | 3290m<br>1560s<br>1600m<br>1455s |
| Vitaletheine V$_4$ | 710w | | 3080s<br>1530m | | | 3290s<br>1560s<br>1253m<br>1650s<br>956m |
| Benzyl derivative | 692–570w | | 3308s<br>1542s<br>1635s | | | 3308s<br>1542s<br>1253m<br>1684s |
| bis-(CBZ)-β-alethine | | | 3345s<br>1545m<br>1640s | | | 3345s<br>1535s<br>1270m<br>1682s |
| β-alethine | 660w | | 3250w<br>1555w–s<br>1286m<br>1620s | | | 3270v<br>2970s–w<br>1462s<br>1620s<br>1128s |
| | a<br>S—CH$_2$ | b<br>CH$_2$—N | c<br>H—N—C=O | d<br>O=C—CH$_2$ | e<br>CH$_2$—N | f<br>—N—H |

*β-alethine was reduced with REDUCTACRYL* (a proprietary reducing agent available from Calbiochem, San Diego, CA, USA) in the presence of ZnO to form β-alethine. The latter reacted with I$_2$ to provide a third reference compound, probably the sulfenyl iodide.

Vitaletheine V$_4$ and vitalethine were unique in that resonances associated with the moiety "f" above disappeared when the compounds melted and decomposed at 233–235° C. (uncorrected) and 242° C., respectively, presumably due to loss of CO$_2$. In vitaletheine V$_4$, these losses occurred without concomitant losses in the regions designating a (—C—O—)$_y$ polymer; thus the decarboxylated form of Vitaletheine V$_4$ appeared to be an oligomer of β-aletheine similar to the undecarboxylated polymer, but lacking the carboxy moieties.

Peaks for Vitalethine: 3290m, 3170w with shoulder at 3100, 2990m, 1660s, 1600w, 1565m, 1455s, 1410w with 1400 shoulder, 1330w with 1310 shoulder, 1260m with 1230 shoulder, 1190w, 1135m, 1100m with 1090 shoulder, 1030m–s, 955m.

Peaks for heated Vitalethine: 3120s (broad), 1655s, 1550m, 1405s with shoulders at 1450 and 1390.

The IR spectrum of vitaletheine $V_4$, following, was shifted by exchanging acetonitrile for water of hydration in the complex.

Peaks for Vitaletheine $V_4$: 3290s, 3080s/broad to 2500, 1650s, 1560s, 1530m, 1453w, 1417w, 1393w, 1346w, 1318w, 1253m, 1190s, 1170s, 1115w/shoulder, 1040s, 1030s, 956m, 790m with shoulder, 709w/broad, 612m/sharp, 526m. These shifts approximated those observed in the spectrum of β-alethine upon neutralization, below.

β-alethine was unusual in that changes in pH, i.e., neutralization with $Ca(OH)_2$, caused pronounced shifts in the positions and intensities of bands.

Peaks (HCl salt): 3270s, 3170s, 2970s, 2700w, 2550w, 2020w, 1657s, 1595m, 1560s, 1450s, 1409m, 1390w, 1354w, 1325m, 1300w, shoulder/1252m/shoulder, 1188m, 1129m, 1097m, 1079w, 1030w, 950w, 905w, 829m.

Peaks (neutralized): 3250w, 3180w, 2940m/broad, 2375s, 2230s, 2157s, 1936w, 1620s, 1555w, 1462s, 1432 shoulder, 1400m, 1342m, 1286m, 1217m, 1188m, 1128s, 1020m, 810w, 719m, 660w.

The benzyl derivative displayed considerable homology with vitaletheine $V_4$.

Peaks: 3308s, 3060w, 2942w, 1684s, 1635s, 1542s, 1447m, 1380w, 1335w, 1286w, 1253m, 1193s, 1170 shoulder, 1080m, 1040m, 980w, 738m, 692m, 609m, 550w.

Bis-(CBZ)-β-alethine displayed little of the C—O resonances around 1200 observed in vitaletheine $V_4$ and the benzyl derivative. Peaks: 3345s, 3310s, 1682s, 1640s, 1545m shoulder, 1535s, 1450w, 1427w, 1375w, 1332m, 1270m, 1231m, 1178w, 1120w, 1030m/broad.

In the following Examples, all cells were cultured at about 37° C. for the specified time.

EXAMPLE VI
Adaptation of Human Natural Killer (NK) Cells to Culture

Human NK cells were purified as described in *J.Exp.Med.* 169: 99–113, 1989. A standard culture medium for the cells was prepared, comprising RPMI 1640 (Rosewell Park Memorial Institute, from Whittaker M. A. Bioproducts, Walkersville, Md., USA) containing 10% human AB- sera, penicillin (100 U/ml) and streptomycin (100 Ag/ml), which served as the control medium. Experimental media were prepared by adding 25 μl/ml of an appropriate aqueous dilution of

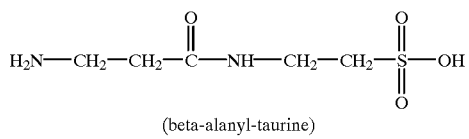

(beta-alanyl-taurine)

to obtain the following final concentrations in separate aliquots of medium containing cells otherwise identical with the controls: 0.1 fg/ml, 1 fg/ml, 10 fg/ml, 100 fg/ml, 1 pg/ml, and 10 pg/ml.

Purified cells ($1\times10^6$) were seeded and incubated in the control and test media at 37° C. under 5% $CO_2$. Cells were counted, and checked for viability daily by monitoring trypan blue (0.1% in phosphate buffered saline) exclusion, and the media containing the same beta-alanyl-taurine concentration were changed every two days to maintain physiological pH and to remove waste products from the cells.

Dramatic stabilization of the NK cell population in culture was observed with beta-alanyl-taurine. By day five, no cells survived in the unsupplemented, i.e., control medium. In media containing beta-alanyl-taurine 70 to 80% of the cells survived for more than a week. Although the extremes of the effective concentration were not defined in this particular experiment, two doses of beta-alanyl-taurine were selected for further study.

The results of the viability tests are summarized in Table I, following:

TABLE 1

| Day | No $V_4$ | 1 fg $V_4$/ml | 1 pg $V_4$/ml |
| --- | --- | --- | --- |
| 0 | 98 ± 2 | 98 ± 2 | 99 ± 2 |
| 1 | 96 ± 1.5 | 98 ± 2 | 99 ± 2.5 |
| 2 | 45 ± 1.8 | 97 ± 1.5 | 98 ± 3 |
| 3 | 30 ± 1.5 | 98 ± 2.5 | 98 ± 2 |
| 4 | 15 ± 0.5 | 97 ± 3 | 97 ± 3 |
| 5–20 | 0 ± 0 | 97 ± 3 | 97 ± 3 |

Beta-alanyl-taurine at concentrations of 1 fg/ml and 1 pg/ml stabilized between 70 and 80% of the cells in culture for an entire month, at which time the cells were frozen for forthcoming functional studies. No cells remained in control cultures, i.e., those lacking vitaletheine $V_4$, by day 6 of the study. Unlike the control cells whose ability to exclude trypan blue dropped precipitously from the first day in culture, 97±3% of the cells in the beta-alanyl-taurine-supplemented media were viable after 30 days in culture, i.e., they excluded the dye.

EXAMPLE VII
Vitaletheine Modulators Substitute for Erythropoietin

The early cell progenitors of red blood cells in erythropoiesis (BFU-E), like the later erythroid progenitors (CFU-E), are dependent upon the presence of erythropoietin in liquid culture media to maintain their proliferative potential (Dessypris, E. N., and Krantz, S. B., 1984, *Br. J. Haematol.* 56: 295–306, incorporated herein by reference).

Human bone marrow cells were obtained as surplus from experiments performed on material aspirated from normal volunteers with IRB approval and informed written consent. Peripheral blood cells were obtained from commercially purchased buffy coats or surgical waste (umbilical cord blood). Mouse bone marrow was flushed from femurs and obtained as surplus from experiments performed on C57B1/6 mice with animal committee approval. Human light density cells were separated by centrifugation over Ficoll-daitrizoate (SG 1.075) and depleted of adherent cells by incubation on serum coated plastic. Mouse cells were used without further fractionation. Cells were suspended at a concentration of 1 to 3 million cells per ml of Iscove's medium (IMDM) supplemented with 10% heat-inactivated fetal calf serum (FCS) with varying concentrations of vitalethine or vitaletheine $V_4$. One unit per ml of erythropoietin and medium without added factors served as positive and negative controls. Initial incubations were carried out for 18 hours at 37° C. Cell suspensions were then pelleted and washed, and the cells were resuspended in culture medium for plasma clot cultures similar to that previously described (Dessypris, E. N., Clark, D. A., McKee, L. C., and Krantz, S. B., 1983, *N. Enal. J. Med.* 309: 690–693, incorporated herein by reference) except that fibrinogen was omitted, fetal calf serum replaced human (AB) serum, and human (AB) plasma replaced bovine plasma. The erythropoietin concentration for cultures of CFU-E was one unit per ml and for BFU-E was 3 units per ml. Cultures were continued for the following periods: mouse and human CFU-E for two and seven days, respectively; and mouse and human BFU-E cultures for seven and fourteen days, respectively. Cultures were fixed, harvested, and stained for hemoglobin with benzidine, and scored as previously described (supra).

Low concentrations of vitalethine (1 to 100 fg/ml) sustain the proliferative potential of BFU-E initially deprived of erythropoietin (FIG. 1a). Colony formation from human BFU-E initially deprived of erythropoietin (lower square) are increased by vitalethine to levels (broken lines) initially containing erythropoietin, but lacking vitalethine (upper square). Colony formation from the early murine progenitors not exposed to vitalethine, and either initially exposed to or initially deprived of erythropoietin are represented by upper and lower triangles, respectively. Vitalethine, depending upon concentration, either enhances or minimizes erythropoiesis from the CFU-E progenitors (solid line). Although late erythroid progenitors are similarly affected by low concentrations of vitalethine, murine CFU-E are influenced more dramatically by higher concentrations of vitalethine; vitalethine from about 100 fg to 1 pg/ml minimizes colony formation, while still higher concentrations (from 10 pg vitalethine/ml) enhance erythropoiesis (FIG. 1a). Vitaletheine $V_4$ (100 fg/ml and higher concentrations) produces a stimulation of colony formation from the CFU-E similar to that produced with high pg/ml concentrations of vitalethine (FIG. 1a). Preformed vitaletheine $V_4$ stimulates colony formation synergistically with erythropoietin (FIG. 1b) at much lower concentrations (from about 10 fg vitaletheine $V_4$/ml) than the higher concentrations of vitalethine (from about 10 pg/ml) necessary for a similar response (1a). Bars are standard error of the mean.

EXAMPLE VIII
Influence of Metal Cations on Deblocking Reactions

The procedure in Example IIA was followed except that magnesium or calcium ions were substituted for zinc ions in maintaining the pH of the reaction. The use of calcium or zinc cations resulted in benzyl derivatives of vitalethine, whereas the use of magnesium salts in this procedure resulted in a cleavage of the N,N'-bis-carbobenzoxy-blocked beta-alethine (benzyl-V-S-S-V-benzyl) at the benzyl ester bond, and the recovery of, the corresponding cyclic urethane of Formula IIf. The production of this cyclic urethane in the presence of magnesium ions was confirmed by IR analysis (unillustrated data), and by NMR analysis of the product of an intramolecular condensation** of the two cyclic urethane moieties in $D_2O$. The rearrangement reactions described herein are summarized as follows:

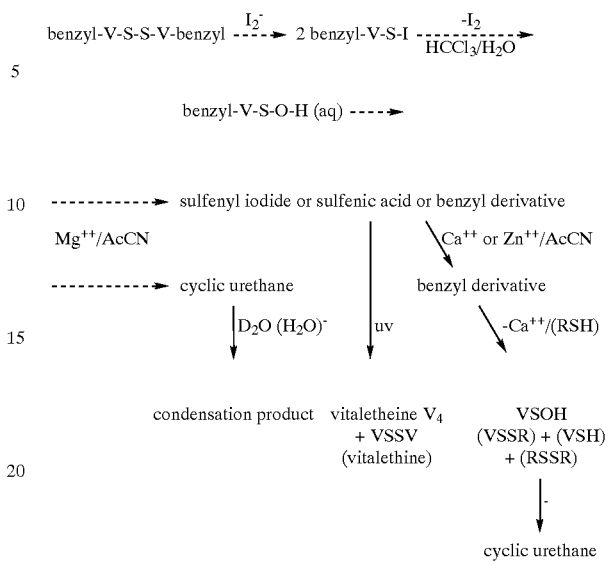

Similar theoretical rearrangements of other compounds to reportedly labile intermediates have been proposed by others, incorporated herein by reference as indicated. Substitution with the chemically similar nucleophiles (O, N, NH, or S) as described in Formula I are contemplated to produce analogous rearrangement products.

EXAMPLE IX
Theoretical Activation of a Benzyl Derivative

Intracellular concentrations of $Mg^{++}$ are mM, and $Ca^{++}$ concentrations are known to range from less than micromolar within the resting cell to over mM in the plasma. Since the calcium salt of a benzyl derivative (according to Example IIA and VII) and vitalethine have been shown to have similar biological activities and potencies (data not shown), activation of a benzyl derivative to a sulfenic acid of vitaletheine is theorized to involve the enzymic ionic pumps within the cell, following:

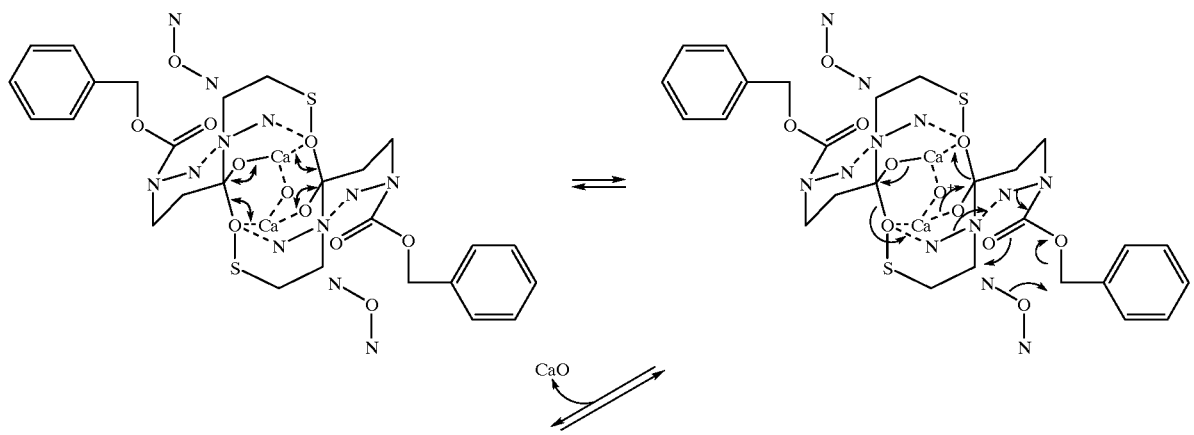

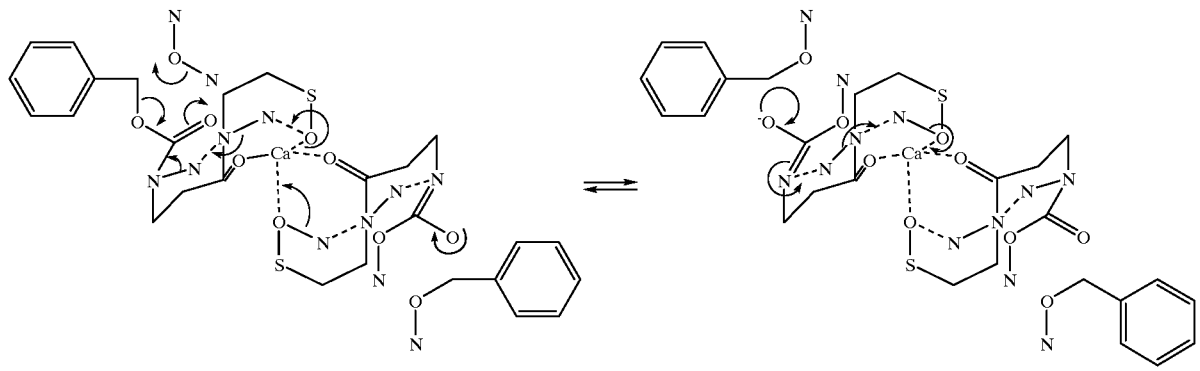

What is claimed is:

1. A method of delaying cell senescence in vitro comprising contacting cells in culture in a culture medium with a senescence-delaying amount of a compound of the formula:

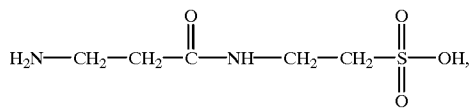

or biologically compatible halt thereof.

2. A method of delaying cell senescence in vitro comprising contacting cells in culture in a culture medium with a senescence-delaying amount of a compound of the formula

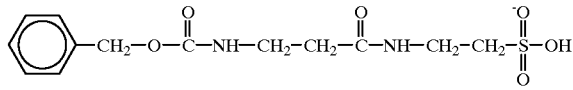

or biologically compatible salt thereof.

3. A method of delaying cell senescence in vitro comprising contacting cells in culture in a culture medium with a senescence-delaying amount of a sulfonic acid compound, or a biologically compatible salt thereof, said compound being produced by a process comprising:
   (i) coupling b-alanine whose terminal amine is protected with a CBZ group to N-hydroxysuccinimide to produce an active, soluble b-alanine ester of N-hydroxysuccinimide,
   (ii) coupling two active esters resulting from (i) to cystamine to produce a CBZ-protected b-alethine having an internal disulfide bond, whose terminal amines are protected by CBZ protecting groups,
   (iii) isolating and purifying the CBZ-protected b-alethine,
   (iv) reacting the recovered CBZ-protected b-alethine with iodine to oxidize the disulfide bond in the CBZppro-tected b-alethine, and
   (v) irradiating the product of (iv) with UV radiation to remove the CBZ-protecting group to produce the sulfonic acid compound.

4. A method of delaying cell senescence in vitro comprising contacting cells in culture in a culture medium with a senescence-delaying amount of a sulfonic acid compound, or a biologically compatible salt thereof, said compound being produced by a process comprising:
   (i) coupling b-alanine whose terminal amine is protected with a CBZ group to N-hydroxysuccinimide to produce an active, soluble b-alanine ester of N-hydroxysuccinimide,
   (ii) (ii) coupling two active esters resulting from (i) to cystamine to produce a CBZ-protected b-alethine having an internal disulfide bond, whose terminal amines are protected by CBZ protecting groups,
   (iii) isolating and purifying the CBZ-protected b-alethine, and
   (iv) reacting the recovered CBZ-protected b-alethine with iodine to oxidize the disulfide bond in the CBZ-Protected b-alethine thereby producing the sulfonic acid compound.

5. A method of increasing the number population doublings achievable by cells in culture in vitro comprising contacting said cells at an early point in the life-cycle thereof with an amount of a sulfonic acid compound sufficient to increase the number of population doublings, or a biologically compatible salt thereof, said compound being produced by a process comprising:
   (i) coupling b-alanine whose terminal amine is protected with a CBZ group to N-hydroxysuccinimide to produce an active, soluble b-alanine ester of N-hydroxysuccinimide,
   (ii) coupling two active esters resulting from (i) to cystamine to produce a CBZ-protected b-alethine having an internal disulfide bond, whose terminal amines are protected by CBZ protecting groups,
   (iii) isolating and purifying the CBZ-protected b-alethine,
   (iv) reacting the recovered CBZ-protected b-alethine with iodine to oxidize the disulfide bond in the CBZppro-tected b-alethine, and
   (v) irradiating the product of (iv) with UV radiation to remove the CBZ-protecting group to produce the sulfonic acid compound.

6. A method of increasing the number population doublings achievable by cells in culture in vitro comprising contacting said cells at an early point in the life-cycle thereof with an amount of a sulfonic acid compound sufficient to increase the number of population doublings, or a biologically compatible salt thereof, said compound being produced by a process comprising:
   (i) coupling b-alanine whose terminal amine is protected with a CBZ group to N-hydroxysuccinimide to produce an active, soluble b-alanine ester of N-hydroxysuccinimide,
   (ii) (ii) coupling two active esters resulting from (i) to cystamine to produce a CBZ-protected b-alethine having an internal disulfide bond, whose terminal amines are protected by CBZ protecting groups, (iii) isolating and purifying the CBZ-protected b-alethine, and (iv) reacting the recovered CBZ-protected b-alethine with iodine to oxidize the disulfide bond in the CBZ-protected b-alethine thereby producing the sulfonic acid compound.

7. A method of optimizing growth and maturation of cells in culture in vitro comprising contacting said cells with an amount of a sulfonic acid compound, or a biologically compatible salt thereof, sufficient to optimize said growth and maturation, said compound being produced by a process comprising:

(i) coupling b-alanine whose terminal amine is protected with a CBZ group to N-hydroxysuccinimide to produce an active, soluble b-alanine ester of N-hydroxysuccinimide, (ii) coupling two active esters resulting from (i) to cystamine to produce a CBZ-protected b-alethine having an internal disulfide bond, whose terminal amines are protected by CBZ protecting groups, (iii) isolating and purifying the CBZ-protected b-alethine, (iv) reacting the recovered CBZ-protected b-alethine with iodine to oxidize the disulfide bond in the CBZppro-tected b-alethine, and (v) irradiating the product of (iv) with UV radiation to remove the CBZ-protecting group to produce the sulfonic acid compound, wherein said contacting is effected at a time prior to the onset of senescence of said cells.

8. A method of optimizing growth and maturation of cells in culture in vitro comprising contacting said cells with an amount of a sulfonic acid compound, or a biologically compatible salt thereof, sufficient to optimize said growth and maturation, said compound being produced by a process comprising:

(i) coupling b-alanine whose terminal amine is protected with a CBZ group to N-hydroxysuccinimide to produce an active, soluble b-alanine ester of N-hydroxysuccinimide, (ii) (ii) coupling two active esters resulting from (i) to cystamine to produce a CBZ-protected b-alethine having an internal disulfide bond, whose terminal amines are protected by CBZ protecting groups, (iii) isolating and purifying the CBZ-protected b-alethine, and (iv) reacting the recovered CBZ-protected b-alethine with iodine to oxidize the disulfide bond in the CBZ-protected b-alethine thereby producing the sulfonic acid compound, wherein said contacting is effected at a time prior to the onset of senescence of said cells.

9. A method for increasing the number of population doublings achievable by cells in culture in vitro comprising contacting said cells at an early point in the life-cycle thereof with an amount of a compound, or a biologically compatible salt thereof, of the Formula

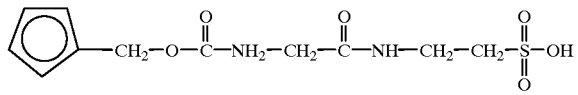

sufficient to increase the number of population doublings.

10. A method for increasing the number of population doublings achievable by cells in culture in vitro comprising contacting said cells at an early point in the life-cycle thereof with an amount of a compound, or a biologically compatible salt thereof, of the Formula

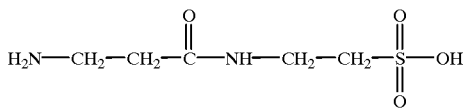

sufficient to increase the number of population doublings.

11. The method as in one of claim 5, 6, 9 or 10 wherein said cells are human cells and the number of population doublings is increased at least two fold.

12. A method of optimizing growth and maturation of cells in culture in vitro comprising contacting said cells with an amount of a compound, or a biologically compatible salt thereof, of the Formula

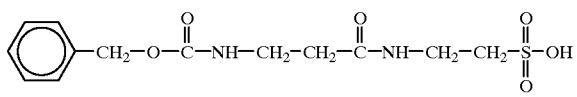

sufficient to optimize said growth and maturation.

13. A method of optimizing growth and maturation of cells in culture in vitro comprising contacting said cells with an amount of a compound, or a biologically compatible salt thereof, of the Formula

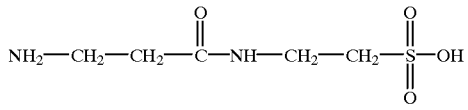

sufficient to optimize said growth and maturation.

14. The method as in one of claim 1, 2, 3, 4, 7, 8, 12 or 13 wherein said cells are mammalian cells selected from the group consisting of organs, glandular, reproductive, lymph node, bone, cartilage, interstitial and blood cells.

* * * * *